United States Patent
Skakoon et al.

(10) Patent No.: US 7,235,084 B2
(45) Date of Patent: Jun. 26, 2007

(54) DEEP ORGAN ACCESS DEVICE AND METHOD

(75) Inventors: James G. Skakoon, St. Paul, MN (US); Robert Wharen, Ponte Vendra Beach, FL (US); Matthew S. Solar, Indialantic, FL (US); Kari Parmer, Melbourne, FL (US); Rudy A. Mazzocchi, Indian Harbor Beach, FL (US); John David, Malabar, FL (US); Frank Murdock, Indialantic, FL (US); David Hatcher, Palm Bay, FL (US); Thomas I. Miller, Palm Bay, FL (US); Timothy Alan Parmer, Melbourne, FL (US); Charles L. Truwit, Wayzata, MN (US)

(73) Assignees: Image-Guided Neurologics, Inc., Melbourne, FL (US); Mayo Foundation for Medical Education and Research, Rochester, MN (US)

( * ) Notice: Subject to any disclaimer, the term of this patent is extended or adjusted under 35 U.S.C. 154(b) by 564 days.

(21) Appl. No.: 10/175,668

(22) Filed: Jun. 20, 2002

(65) Prior Publication Data

US 2002/0156372 A1 Oct. 24, 2002

Related U.S. Application Data

(63) Continuation of application No. 09/828,451, filed on Apr. 6, 2001.

(60) Provisional application No. 60/195,663, filed on Apr. 7, 2000.

(51) Int. Cl.
*A61B 19/00* (2006.01)

(52) U.S. Cl. .................................... 606/130; 606/129

(58) Field of Classification Search ............... 606/129, 606/130, 170, 108, 87; 600/235, 431, 426; 264/271
See application file for complete search history.

(56) References Cited

U.S. PATENT DOCUMENTS

| 1,129,333 A | 2/1915 | Clarke |
| 1,664,210 A | 3/1928 | Hall |
| 2,119,649 A | 6/1938 | Roosen |

(Continued)

FOREIGN PATENT DOCUMENTS

DE         3108766         9/1982

(Continued)

OTHER PUBLICATIONS

"Cross-Hairs Kit", *Elekta Instruction for Use Brochure*, 4 pgs.

(Continued)

*Primary Examiner*—Justine R. Yu
*Assistant Examiner*—Annette Dixon
(74) *Attorney, Agent, or Firm*—Schwegman, Lundberg, Woessner & Kluth, P.A.

(57) ABSTRACT

Devices and methods provide accurate targeting, placement, and/or stabilization of an electrode or other instrument(s) into the brain or other body organ, such as to treat severe tremor or other neurological disorders. Targeting is performed using any form of image-guidance, including real-time MRI, CT, or frameless surgical navigation systems.

45 Claims, 36 Drawing Sheets

U.S. PATENT DOCUMENTS

| | | |
|---|---|---|
| 2,135,160 A | 11/1938 | Beekhuis |
| 3,017,887 A | 1/1962 | Heyer |
| 3,055,370 A | 9/1962 | McKinney et al. |
| 3,055,371 A | 9/1962 | Kulick et al. |
| 3,135,263 A | 6/1964 | Connelley, Jr. |
| 3,223,087 A | 12/1965 | Vladyka et al. |
| 3,273,559 A | 9/1966 | Evans |
| 3,282,152 A | 11/1966 | Myer |
| 3,402,710 A | 9/1968 | Paleschuck |
| 3,444,861 A | 5/1969 | Schulte |
| 3,457,922 A | 7/1969 | Ray |
| 3,460,537 A | 8/1969 | Zeis |
| 3,508,552 A | 4/1970 | Hainault |
| 3,672,352 A | 6/1972 | Summers |
| 3,760,811 A | 9/1973 | Andrew |
| 3,893,449 A | 7/1975 | Lee et al. |
| 4,040,427 A | 8/1977 | Winnie |
| 4,230,117 A | 10/1980 | Anichkov |
| 4,265,252 A | 5/1981 | Chubbuck et al. |
| 4,312,337 A | 1/1982 | Donohue |
| 4,328,813 A | 5/1982 | Ray |
| 4,341,220 A | 7/1982 | Perry |
| 4,345,606 A | 8/1982 | Littleford |
| 4,350,159 A | 9/1982 | Gouda |
| 4,355,645 A | 10/1982 | Mitani et al. |
| 4,386,602 A | 6/1983 | Sheldon et al. |
| 4,448,195 A | 5/1984 | LeVeen et al. |
| 4,463,758 A | 8/1984 | Patil et al. |
| 4,475,550 A | 10/1984 | Bremer et al. |
| 4,483,344 A | 11/1984 | Atkov et al. |
| 4,571,750 A | 2/1986 | Barry |
| 4,572,198 A | 2/1986 | Codrington |
| 4,579,120 A | 4/1986 | MacGregor |
| 4,592,352 A | 6/1986 | Patil |
| 4,598,708 A | 7/1986 | Beranek |
| 4,608,977 A | 9/1986 | Brown |
| 4,617,925 A | 10/1986 | Laitinen |
| 4,618,978 A | 10/1986 | Cosman |
| 4,629,451 A | 12/1986 | Winters et al. |
| 4,638,798 A | 1/1987 | Shelden et al. |
| 4,660,563 A | 4/1987 | Lees |
| 4,665,928 A | 5/1987 | Linial et al. |
| 4,699,616 A | 10/1987 | Nowak et al. |
| 4,706,665 A | 11/1987 | Gouda |
| 4,733,661 A | 3/1988 | Palestrant |
| 4,755,642 A | 7/1988 | Parks |
| 4,791,934 A | 12/1988 | Brunnett |
| 4,793,355 A | 12/1988 | Crum et al. |
| 4,805,615 A | 2/1989 | Carol |
| 4,805,634 A | 2/1989 | Ullrich et al. |
| 4,807,620 A | 2/1989 | Strul et al. |
| 4,809,694 A | 3/1989 | Ferrara |
| 4,824,436 A | 4/1989 | Wolinsky |
| 4,826,487 A | 5/1989 | Winter |
| 4,869,247 A | 9/1989 | Howard, III et al. |
| 4,883,053 A | 11/1989 | Simon |
| 4,896,673 A | 1/1990 | Rose et al. |
| 4,902,129 A | 2/1990 | Siegmund et al. |
| 4,922,924 A | 5/1990 | Gambale et al. |
| 4,955,891 A | 9/1990 | Carol |
| 4,957,481 A | 9/1990 | Gatenby |
| 4,986,280 A | 1/1991 | Marcus et al. |
| 4,986,281 A | 1/1991 | Preves et al. |
| 4,989,608 A | 2/1991 | Ratner |
| 4,991,579 A | 2/1991 | Allen |
| 4,998,938 A | 3/1991 | Ghajar et al. |
| 5,006,122 A | 4/1991 | Wyatt et al. |
| 5,024,236 A | 6/1991 | Shapiro |
| 5,027,818 A | 7/1991 | Bova et al. |
| 5,030,223 A | 7/1991 | Anderson et al. |
| 5,050,608 A | 9/1991 | Watanabe et al. |
| 5,052,329 A | 10/1991 | Bennett |
| 5,054,497 A | 10/1991 | Kapp et al. |
| 5,057,084 A | 10/1991 | Ensminger et al. |
| 5,057,106 A | 10/1991 | Kasevich et al. |
| 5,065,761 A | 11/1991 | Pell |
| 5,078,140 A | 1/1992 | Kwoh |
| 5,078,142 A | 1/1992 | Siczek et al. |
| 5,080,662 A | 1/1992 | Paul |
| 5,087,256 A | 2/1992 | Taylor et al. |
| 5,099,846 A | 3/1992 | Hardy |
| 5,102,402 A | 4/1992 | Dror et al. |
| 5,116,344 A | 5/1992 | Sundqvist |
| 5,116,345 A * | 5/1992 | Jewell et al. ............... 606/130 |
| 5,120,322 A | 6/1992 | Davis et al. |
| 5,125,888 A | 6/1992 | Howard et al. |
| 5,142,930 A | 9/1992 | Allen et al. |
| 5,143,086 A | 9/1992 | Duret et al. |
| 5,154,179 A | 10/1992 | Ratner |
| 5,154,723 A | 10/1992 | Kubota et al. |
| 5,163,430 A | 11/1992 | Carol |
| 5,166,875 A | 11/1992 | Machida |
| 5,171,217 A | 12/1992 | March et al. |
| 5,174,297 A | 12/1992 | Daikuzono |
| 5,186,174 A | 2/1993 | Schlondorff et al. |
| 5,201,742 A | 4/1993 | Hasson |
| 5,207,223 A | 5/1993 | Adler |
| 5,207,688 A | 5/1993 | Carol |
| 5,211,165 A | 5/1993 | Dumoulin et al. |
| 5,221,264 A | 6/1993 | Wilk et al. |
| 5,222,499 A | 6/1993 | Allen et al. |
| 5,230,338 A | 7/1993 | Allen et al. |
| 5,230,623 A | 7/1993 | Guthrie et al. |
| 5,246,448 A | 9/1993 | Chang |
| 5,257,998 A | 11/1993 | Ota et al. |
| 5,263,939 A | 11/1993 | Wortrich |
| 5,263,956 A | 11/1993 | Nobles |
| 5,267,970 A | 12/1993 | Chin et al. |
| 5,269,305 A | 12/1993 | Corol |
| 5,279,309 A | 1/1994 | Taylor et al. |
| 5,279,575 A | 1/1994 | Sugarbaker |
| 5,290,266 A | 3/1994 | Rohling et al. |
| 5,291,890 A | 3/1994 | Cline et al. |
| 5,300,080 A | 4/1994 | Clayman et al. |
| 5,305,203 A | 4/1994 | Raab |
| 5,309,913 A | 5/1994 | Kormos et al. |
| 5,330,485 A | 7/1994 | Clayman et al. |
| 5,354,283 A | 10/1994 | Bark et al. |
| 5,361,763 A | 11/1994 | Kao et al. |
| 5,366,446 A | 11/1994 | Tal et al. |
| 5,375,588 A | 12/1994 | Yoon |
| 5,375,596 A | 12/1994 | Twiss et al. |
| 5,380,302 A | 1/1995 | Orth |
| 5,383,454 A | 1/1995 | Bucholz |
| 5,387,220 A | 2/1995 | Pisharodi |
| 5,423,848 A | 6/1995 | Washizuka et al. |
| 5,445,166 A | 8/1995 | Taylor |
| 5,452,720 A | 9/1995 | Smith et al. |
| 5,464,446 A | 11/1995 | Dressen et al. |
| 5,470,307 A | 11/1995 | Lindall |
| 5,474,564 A | 12/1995 | Clayman et al. |
| 5,483,961 A | 1/1996 | Kelly et al. |
| 5,494,034 A | 2/1996 | Schlondorff et al. |
| 5,494,655 A | 2/1996 | Rocklage et al. |
| 5,515,160 A | 5/1996 | Schulz et al. |
| 5,517,990 A | 5/1996 | Kalfas et al. |
| 5,528,652 A | 6/1996 | Smith et al. |
| 5,572,999 A | 11/1996 | Funda et al. |
| 5,575,798 A | 11/1996 | Koutrouvelis |
| 5,618,288 A | 4/1997 | Calvo |
| 5,622,170 A | 4/1997 | Schulz |
| 5,638,819 A | 6/1997 | Manwaring et al. |
| 5,643,286 A | 7/1997 | Warner et al. |
| 5,647,361 A | 7/1997 | Damadian |

| | | |
|---|---|---|
| 5,658,272 A | 8/1997 | Hasson |
| 5,662,600 A | 9/1997 | Watson et al. |
| 5,667,514 A | 9/1997 | Heller |
| 5,695,501 A | 12/1997 | Carol et al. |
| 5,713,858 A | 2/1998 | Heruth et al. |
| 5,776,064 A | 7/1998 | Kalfas et al. |
| 5,776,143 A | 7/1998 | Adams |
| 5,776,144 A * | 7/1998 | Leysieffer et al. .......... 606/130 |
| 5,810,712 A | 9/1998 | Dunn |
| 5,817,106 A | 10/1998 | Real |
| 5,833,627 A | 11/1998 | Shmulewitz et al. |
| 5,843,150 A | 12/1998 | Dressen et al. |
| 5,851,183 A | 12/1998 | Bucholz |
| 5,865,842 A | 2/1999 | Knuth et al. |
| 5,871,445 A | 2/1999 | Bucholz |
| 5,873,822 A | 2/1999 | Ferre et al. |
| 5,891,034 A | 4/1999 | Bucholz |
| 5,891,157 A | 4/1999 | Day et al. |
| 5,927,277 A * | 7/1999 | Baudino et al. ............ 600/386 |
| 5,950,629 A | 9/1999 | Taylor et al. |
| 5,954,687 A | 9/1999 | Baudino |
| 5,957,934 A | 9/1999 | Rapoport |
| 5,964,705 A | 10/1999 | Truwit et al. |
| 5,980,535 A | 11/1999 | Barnett et al. |
| 5,984,930 A * | 11/1999 | Maciunas et al. ........... 606/130 |
| 5,993,463 A * | 11/1999 | Truwit ........................ 606/130 |
| 6,006,126 A | 12/1999 | Cosman |
| 6,021,343 A | 2/2000 | Foley et al. |
| 6,044,304 A | 3/2000 | Baudino |
| 6,058,323 A | 5/2000 | Lemelson |
| 6,071,288 A | 6/2000 | Carol et al. |
| 6,076,008 A | 6/2000 | Bucholz |
| 6,110,182 A | 8/2000 | Mowlai-Ashtiani |
| 6,117,143 A * | 9/2000 | Hynes et al. ............... 606/130 |
| 6,120,465 A | 9/2000 | Guthrie et al. |
| 6,135,946 A | 10/2000 | Konen et al. |
| 6,179,826 B1 | 1/2001 | Aebischer et al. |
| 6,206,890 B1 | 3/2001 | Truwit |
| 6,210,417 B1 | 4/2001 | Baudino et al. |
| 6,231,526 B1 | 5/2001 | Taylor et al. |
| 6,236,875 B1 | 5/2001 | Bucholz et al. |
| 6,254,532 B1 | 7/2001 | Paolitto et al. |
| 6,257,407 B1 | 7/2001 | Truwit et al. |
| 6,261,300 B1 | 7/2001 | Carol et al. |
| 6,267,769 B1 | 7/2001 | Truwit |
| 6,267,770 B1 | 7/2001 | Truwit |
| 6,282,437 B1 | 8/2001 | Franck et al. |
| 6,290,644 B1 | 9/2001 | Green et al. |
| 6,298,262 B1 | 10/2001 | Franck et al. |
| 6,315,770 B1 | 11/2001 | De la Torre et al. |
| 6,321,104 B1 * | 11/2001 | Gielen et al. ............... 600/378 |
| 6,356,792 B1 | 3/2002 | Errico et al. |
| 6,368,329 B1 | 4/2002 | Truwit |
| 6,482,182 B1 | 11/2002 | Carroll et al. |
| 6,529,765 B1 | 3/2003 | Franck et al. |
| 6,537,232 B1 | 3/2003 | Kucharczyk et al. |
| 6,546,279 B1 | 4/2003 | Bova et al. |
| 6,609,020 B2 | 8/2003 | Gill |
| 6,632,184 B1 | 10/2003 | Truwit |
| 6,662,035 B2 | 12/2003 | Sochor |
| 6,726,678 B1 | 4/2004 | Nelson et al. |
| 6,752,812 B1 | 6/2004 | Truwit |
| 6,773,443 B2 | 8/2004 | Truwit |
| 6,782,288 B2 | 8/2004 | Truwit et al. |
| 6,802,323 B1 | 10/2004 | Truwit et al. |
| 6,902,569 B2 | 6/2005 | Parmer et al. |
| 6,944,895 B2 | 9/2005 | Truwit |
| 2001/0014771 A1 | 8/2001 | Truwit et al. |
| 2001/0027271 A1 | 10/2001 | Franck et al. |
| 2001/0037524 A1 | 11/2001 | Truwit |
| 2002/0019641 A1 | 2/2002 | Truwit |
| 2002/0052610 A1 | 5/2002 | Skakoon et al. |
| 2002/0077646 A1 | 6/2002 | Truwit et al. |
| 2002/0156372 A1 | 10/2002 | Skakoon et al. |
| 2003/0079287 A1 | 5/2003 | Tuiwit |
| 2004/0059260 A1 | 3/2004 | Truwit |
| 2004/0255991 A1 | 12/2004 | Truwit et al. |
| 2004/0260323 A1 | 12/2004 | Truwit et al. |
| 2004/0267284 A1 | 12/2004 | Parmer et al. |
| 2006/0192319 A1 | 8/2006 | Solar |
| 2006/0195119 A1 | 8/2006 | Mazzocchi et al. |

FOREIGN PATENT DOCUMENTS

| | | |
|---|---|---|
| DE | 3937052 | 5/1990 |
| DE | 29612100 | 9/1996 |
| DE | 19726141 | 1/1999 |
| DE | 19826078 | 8/1999 |
| DE | 19808220 | 9/1999 |
| DE | 19820808 | 11/1999 |
| EP | 0386936 | 9/1990 |
| EP | 0427358 | 5/1991 |
| EP | 0609085 | 8/1994 |
| EP | 0724865 A1 | 8/1996 |
| EP | 0832611 A2 | 4/1998 |
| EP | 0904741 A2 | 3/1999 |
| GB | 2237993 | 5/1991 |
| GB | 2329473 | 3/1999 |
| WO | WO-88/09151 | 12/1988 |
| WO | WO-95/22297 A1 | 8/1995 |
| WO | WO-96/10368 A2 | 4/1996 |
| WO | WO-96/33766 | 10/1996 |
| WO | WO-97/03609 A1 | 2/1997 |
| WO | WO-97/21380 A2 | 6/1997 |
| WO | WO-97/42870 | 11/1997 |
| WO | WO-98/17191 A1 | 4/1998 |
| WO | WO-98/25535 A1 | 6/1998 |
| WO | WO-00/01316 A1 | 1/2000 |
| WO | WO-00/18306 A1 | 4/2000 |
| WO | WO-01/24709 A1 | 4/2001 |
| WO | WO-01/49197 A1 | 7/2001 |

OTHER PUBLICATIONS

"CRW™—Tyco Healthcare Radionics", *Tyco Product Brochure*, 7 pgs.

"Fathom Remote Introducer", *Image-Guided Neurologics, Inc.*, CNS Hynes Convention Center,(Oct. 30-Nov. 4, 1999), 2 pgs.

"Leksell Sterotatic System", *Elekta Product Brochure*, 6 pgs.

Franck, J., et al., "microTargeting® Platform System incorprating StarFix™ guidance—User Manual", *micro Targeting®*, 1-44.

Grady, M., et al., "Nonlinear Magnetic Stereotaxis: Three-Dimensional, in vivo Remote Magnetic Manipulation of a Small Object in Canine Brain", *Medical Physics*, 17 (3), (May/Jun. 1990),pp. 405-415.

Hata, N., et al., "Needle Insertion Manipulator for CT—and MR-Guided Stereotactic Neurosurgery", *Interventional MR: Techniques and Clinical Experience*, St. Louis : London : Mosby ; Martin Dunitz, F. Jolesz and I. Young, eds.,(1998), 99-106.

Hirschberg, H., et al., "Image-guided neurosurgery—MR compatible sterotactic equipment", http:www.medinnova.no/English/P51466ster.html, (Mar. 29, 2001), 1 pg.

Leggett, W. B., et al., "Surgical Technology—The Viewing Wand: A New System for Three-Dimensional Computed Tomography-Correlated Intraoperative Localization", *Current Surgery*, (Dec. 1991), 674-678.

Oliver, L., "Cup-And-Ball Chemopallidectomy Apparatus", (1958),p. 401.

Sandeman, D. S., et al., "Advances in image-directed neurosurgery: Preliminary experience with the ISG Viewing Wand compared with the Lesksell G frame", *British Journal of Neurosurgery*, 8, (199),pp. 529-544.

Yeh, H.-S., et al., "Implantation of intracerebral depth electrodes for monitoring seizures using the Pelorus stereotactic system guided by magnetic resonance imaging", *J. Neurosurg.*, 78, (1993),pp. 138-141.

Zinreich, S. J., et al., "Frameless Sterotaxic Integration of CT Imaging Data: Accuracy and Initial Applications", *Radiology*, 188 (3), (1993),pp. 735-742.

Allison, S., et al., "Microchannel Plate Intensifier Response in Transverse Magnetic Field", *Electronic Letters*, 26, (Jun. 7, 1990),770-771.

Drake, J. M., et al., "ISG Viewing Wand System", *Neurosurgery*, 34 (6), (Jun. 1994), 1094-1097.

Dyer, P. V., et al., "The ISG Viewing Wand: an Application to Atlanto-Axial Cervical Surgery Using the Le Fort I Maxillary Osteotomy", *British Journal of Oral and Maxillofacial Surgery*, 33, (1995),370-374.

Gillies, G., et al., "Magnetic Manipulation Instrumentation for Medical Physics Research", *Review of Scientific Instruments*, 65 (3), Review Article,(Mar. 1994),533-562.

Grady, M., et al., "Initial Experimental Results of a New Stereotaxic Hyperthermia System", *American College of Surgeons: 1998 Clinical Congress: Surgical Forum*, 39, (1998),507-509.

Grady, M., et al., "Magnetic Stereotaxis System for Neurosurgical Procedures", *Proc. 37th International Instrumentation Symp.*, San Diego, CA,(May 1991),665-675.

Gray, M., et al., "Magnetic Stereotaxis: A Technique to Deliver Stereotactic Hyperthermia", *Neurosurgery*, 27 (6), Technical Note,(Dec. 1990),pp. 1010-1016.

Grady, M., et al., "Preliminary Experimental Investigation of in vivo Magnetic Manipulation: Results and Potential Application in Hyperthermia", *Medical Physics*, 16 (2), (Mar./Apr. 1989),pp. 263-272.

Howard, M., et al., "Magnetic Movement of a Brain Thermoceptor", *Neurosurgery*, 24 (3), (1989), 444-448.

Howard, M., et al., "Magnetic Neurosurgery", *Stereotactic and Functional Neurosurgery*, 66, (1996),102-107.

Howard, M., et al., "Magnetic Neurosurgery: Image-Guided, Remote-Controlled Movement of Neurosurgical Implants", *Ch. 26 In: Clinical Neurosurgery; Proceedings of the Congress of Neurological Surgeons*, San Francisco, CA,(1995),382-391.

Howard, M., et al., "Review of Magnetic Neurosurgery Research", *J. Image Guided Surgery*, 1, (Nov. 1995),295-299.

Lawson, M., et al., "Near Real-Time Bi-planar Fluoroscopic Tracking System for the Video Tumor Fighter", *SPIE*, 1445, (1991),265-275.

Leggett, W. B., et al., "Surgical Technology—The Viewing Wand: A New System for Three-Dimensional Comuted Tomography-Correlated Intraoperative Localization", *Current Surgery*, (1991),674-678.

Malison, R. T., et al., "Computer-Assisted Coregistration of Multislice SPECT and MR Brain Images by Fixed External Fiducials", *Journal of Computer Assisted Tomography*, 17 (16), (1993),pp. 952-960.

McNeil, R., et al., "Characteristics of an Improved Magnetic-Implant Guidance System", *IEEE Transactions on Biomedical Engineering*, 42 (8), (Aug. 1995), 802-808.

McNeil, R., et al., "Functional Design Features and Initial Performance Characteristics of a Magnetic-Implant Guidance System for Stereotactic Neurosurgery", *IEEE Transactions on Biomedical Engineering*, 42 (8), (1995), 793-801.

Meeker, D., et al., "Optimal Realization of Arbitrary Forces in a Magnetic Stereotaxis System", *IEEE Transactions on Magnetics*, 32 (2), (Mar. 1996), 320-328.

Molloy, J., et al., "Experimental Determination of the Force Required for Insertion of a Thermoseed into Deep Brain Tissues", *Annals of Biomedical Engineering*, 18, (1990), 299-313.

Molloy, J., et al., "Thermodynamics of Movable Inductively Heated Seeds for the Treatment of Brain Tumors", *Medical Physics*, 18 (4), (1991), 794-803.

Quate, E., et al., "Goniometric Motion Controller for the Superconducting Coil in a Magnetic Stereotaxis System", *IEEE Transactions on Biomedical Engineering*, 38 (9), (Sep. 1991), 899-905.

Ramos, P., et al., "Electro-Optic Imaging Chain for a Biplanar Fluroscope for Neurosurgery: Magnetic Field Sensitivity and Contrast Measurements", *Optical Engineering 32* (7), (1993), 1644-1656.

Ramos, P., et al., "Low-Dose, Magnetic Field-Immune, Bi-Planar Fluoroscopy for Neurosurgery", *Proc. SPIE, 1443 (Medical Imaging V: Image Physics)*, (1991),160-170.

Ramos, P., et al., "Microchannel Plate Image Intensifier Electron Dynamics in Magnetic Field", *Electronics Letters*, 27 (18), (Aug. 29, 1991),pp. 1636-1638.

Ritter, R., et al., "Magnetic Sterotaxis: An Application of Magnetic Control Technology to the Needs of Clinical Medicine", *Proc. of the MAG'95 Industrial Conf. and Exhibition*, Technomic Pub. Co., Lancaster, PA., Allaire. P., ed.,(1995),186-193.

Ritter, R., et al., "Magnetic Stereotaxis: Computer-Assisted, Image-Guided Remote Movement of Implants in the Brain", *Ch. 26 In: Computer-Integrated Surgery; Technology and Clinical Applications*, MIT Press, Cambridge, MA., Taylor, R., et al., eds.,(1996), 363-369.

Ritter, R., et al., "Stereotaxie Magnetique: Deplacement D'Implants dans le Cerveau, Assistes par Ordinateur et Guides par Imagerie.", *Innovation et Technologie en Biologie et Medecine*, 13, (1992),437-449.

Sandeman, D. R., et al., "Advances in image-Directed Neurosurgery: Preliminainary Experience With the ISG Viewing Wand Compared With the Leksell G Frame", *British Journal of Neurosurgery*, 8, (199), 529-544.

Szikora, I., et al., "Endovascular Treatment of Experimental Aneurysms with Liquid Polymers: The Protective Potential of Stents", *Neurosurgery*, 38, (Feb. 1996),339-347.

Zinreich, S. J., "Frameless Sterotaxic Integration of CT Imaging Data: Accuracy and Initial Applications", *Radiology*, 188 (3), (1993),735-742.

\* cited by examiner

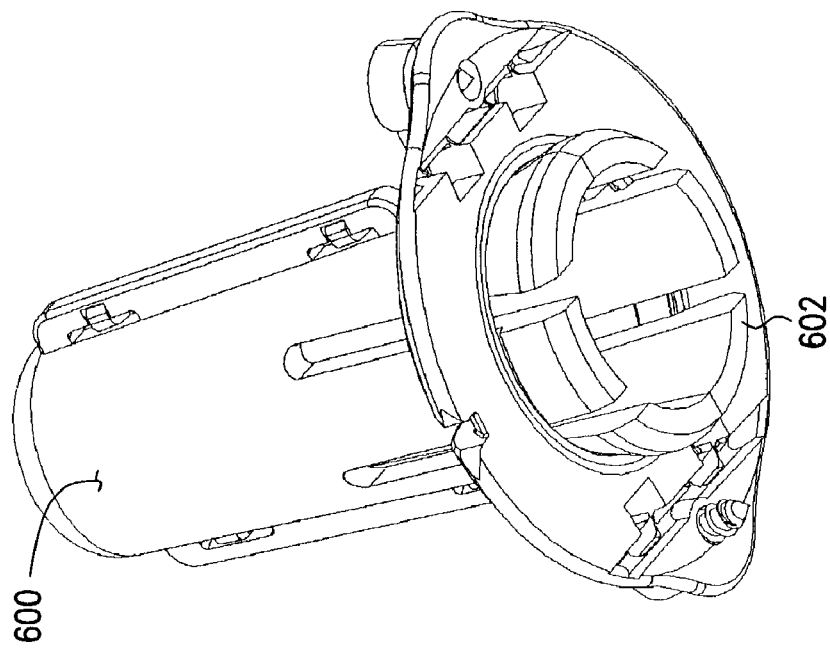
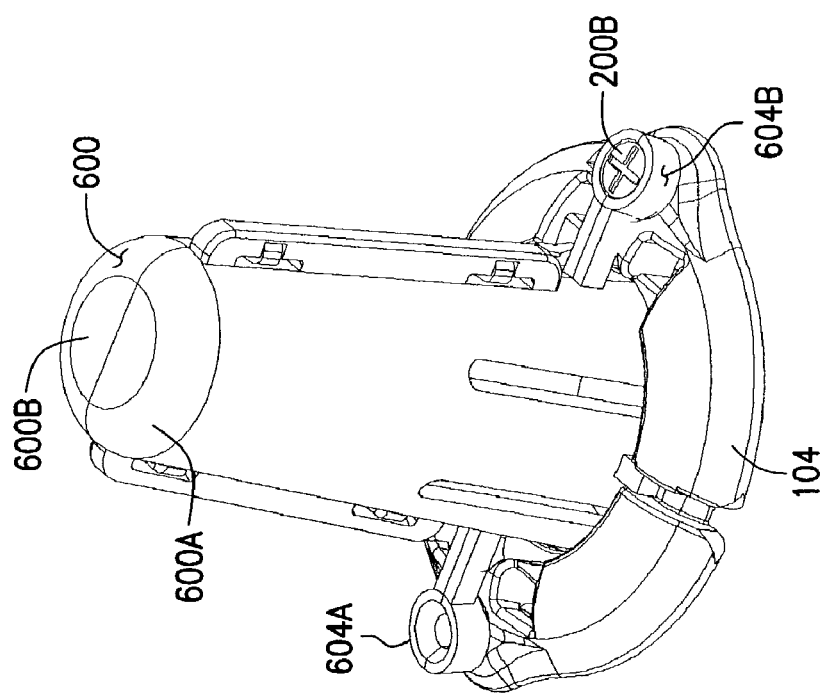

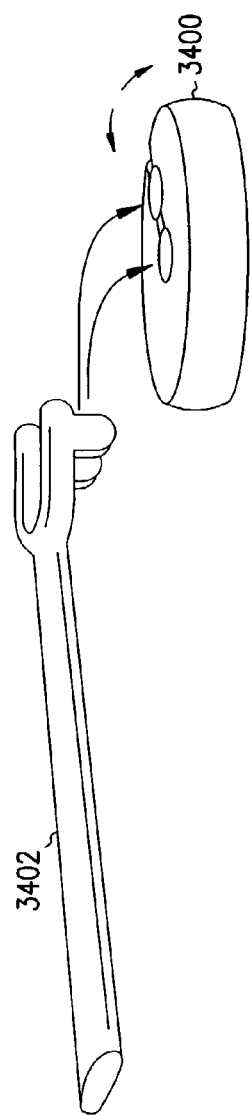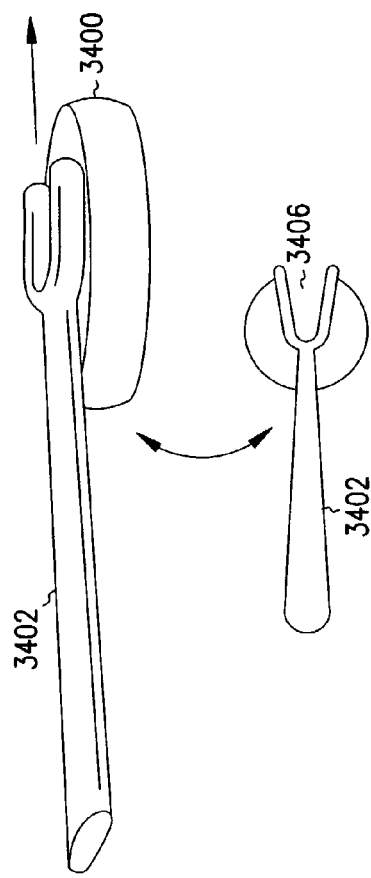
FIG. 34A
FIG. 34B

DEEP ORGAN ACCESS DEVICE AND METHOD

CROSS-REFERENCE TO RELATED APPLICATION

This application is a continuation application of Ser. No. 09/828,451, filed Apr. 6, 2001, entitled: DEEP ORGAN ACCESS DEVICE AND METHOD.

This patent application claims the benefit of priority, under 35 U.S.C. Section 119(e), to U.S. Provisional Patent Application Ser. No. 60/195,663, filed Apr. 7, 2000, the disclosure of which is incorporated herein by reference in its entirety.

FIELD OF THE INVENTION

This document relates generally to, among other things, surgical placement of a medical instrument deeply into an organ, such as a brain, and specifically, but not by way of limitation, to accurate targeting, placement, and/or acute or chronic stabilization of such an instrument.

BACKGROUND

In placing a medical device or instrument deeply into an organ, such as a brain, it is often advantageous to precisely target, place, and then secure the device for a period of time that may be several days or even indefinitely. Examples of such devices include catheters, needles, and drug and biological agent delivery instruments, as well as electrical mapping, stimulating and/or ablation leads.

Targeting such a device is not always an exact science. The target is not always visible from preoperative images. Even when using image-guided minimally invasive techniques, with such imaging modalities magnetic resonance imaging (MRI), computed tomography (CT), frameless surgical navigation systems, and the like, there is often a need for some tweaking or small adjustment in trajectory to accurately hit the target. A single trajectory approach would mean that the need to move the target slightly laterally would require removing the device and then reintroducing it, sometimes as close as 2 mm away from the original entry site.

One approach to positioning an instrument, such as a deep brain stimulation electrode, uses a conventional stereotactic frame system that is secured to the patient. In this approach, preoperative images of the patient are used to determine the proper trajectory to the target, as measured and aligned relative to the frame. Using accessories mounted to the frame, the electrode is aligned and advanced through a burr hole in the skull to the predetermined target. A base is then inserted into and/or around the burr hole. Various "tool holes" and slots in the base are deformed as the base is slid over the electrode. The tool holes in the base are squeezed together as the base is inserted into the burr hole. When the base is released, it springs back outward against the inside diameter of the burr hole. The stereotactic accessories must then be carefully removed while holding the device in place. This step can be clumsy and inexact. If the electrode moves, it must be repositioned. Before securing the carefully-positioned device to the patient, the equipment used to introduce the device and maintain trajectory must be removed. This action can often dislodge the device requiring the entire placement procedure to be repeated. Even after the stereotactic accessories have been removed, the electrode or other device must be secured. This procedure may also cause electrode movement. In one example, a silicone rubber cap is fit into place to capture and protect the electrode. Placing the rubber cap may cause further electrode movement.

One disadvantage of this approach is that the instrument positioning is attempted using only a presumed target location, based on the preoperative images, and not an actual determination of the needed trajectory to the target. Another disadvantage is that the stereotactic frame system is both expensive and unwieldy. Yet another disadvantage is that the electrode may move at any one of several times during the procedure and therefore require repositioning. For these and other reasons, the present inventors have recognized that there is a need for improved targeting, placement, and secure stabilization of a deep brain electrode or other medical instrument.

SUMMARY

This document discusses, among other things a device and method for instrument targeting, placement, and/or stabilization. This system may be used with any instrument, but it is particularly useful with a deep brain neurological stimulation electrode to treat severe tremor or other disorders. The system allows any of a number of imaging modalities, including MRI, CT, and frameless surgical navigation. The MRI environment typically provides both real-time brain images and real-time MRI imaging of trajectory-alignment fiducial markings, although preoperative MRI images of the brain could also be used. The frameless surgical navigation typically uses retrospective brain images (e.g., previously-acquired preoperative MRI images of the brain) and real-time imaging recognition of trajectory-alignment fiducial markings (e.g., using light-emitting diodes, reflective globes, etc.). Both environments, therefore, provide image-guided alignment of the instrument's trajectory to the target location. Such techniques provide accurate placement of the electrode or other medical instrument. It also provides acute and/or chronic stabilization of the instrument. The system includes, among other things, an alignment/targeting system, an instrument introducer system, and a stabilizer system. Other aspects of the present system and methods will become apparent upon reading the following detailed description of the invention and viewing the drawings that form a part thereof.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

FIG. 6 provides two perspective view examples of a base and a burr-hole centering device.

FIG. 34 provides various perspective view examples of another alternate stabilizer and accompanying tool.

DETAILED DESCRIPTION

The following detailed description refers to the accompanying drawings, which form a part of this detailed description and illustrate specific embodiments of the invention. These embodiments are described in sufficient detail to enable those skilled in the art to practice the invention. However, other embodiments may be used, thus structural, logical and electrical changes may be made to this description without departing from the spirit and scope of the invention. The following detailed description is, therefore, not to be taken in a limiting sense, as the scope of the invention is defined only by the appended claims.

One example of trajectory guides for surgical applications is discussed in Truwit et al., International Patent Application No. PCT/US98/10008 (International Publication No. WO 98/51229), which is incorporated herein by reference.

Figure 1:
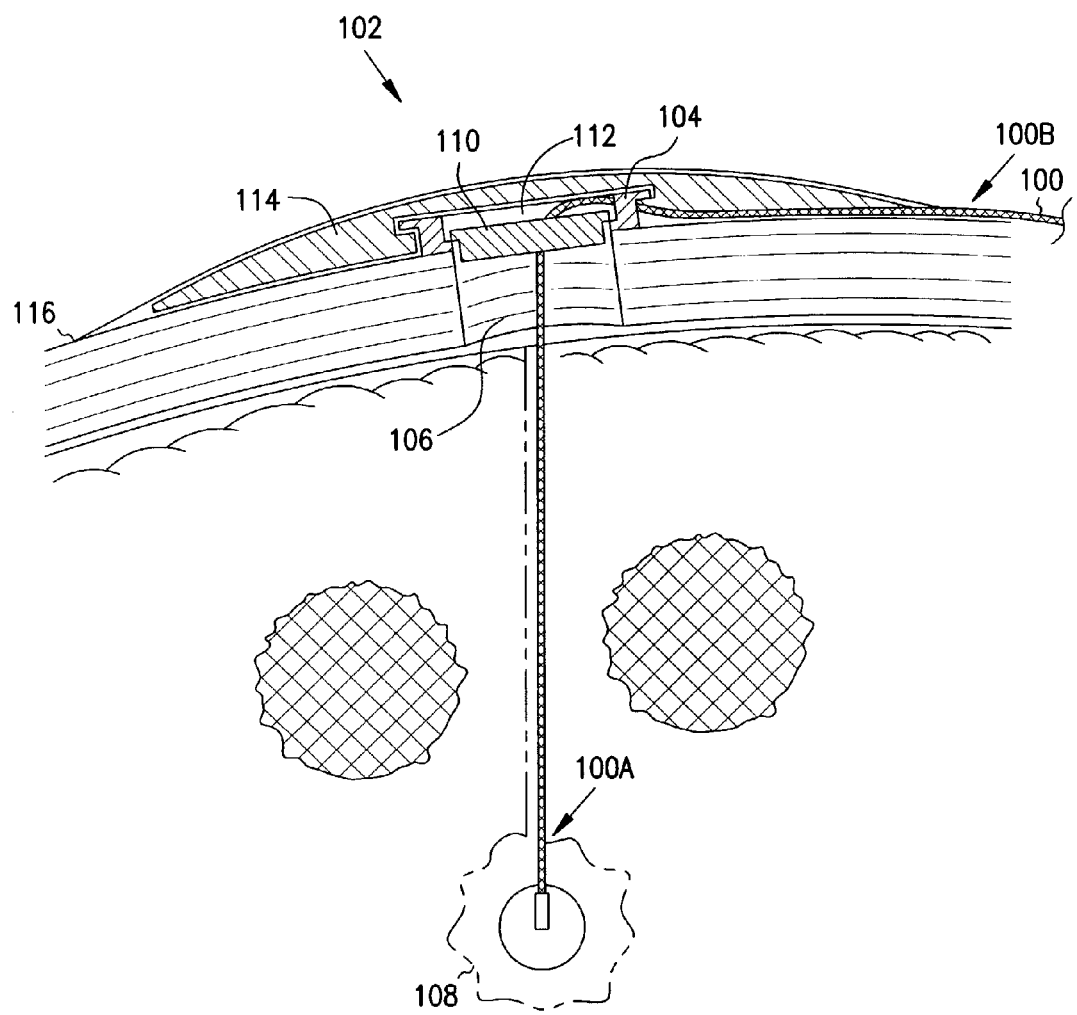
FIG. 1 is a cross-sectional view example of an electrode that has been implanted and secured using the devices and methods discussed herein.

FIG. 1 is a cross-sectional view illustrating an example of a flexible primary medical instrument, such as an implanted deep brain neurostimulator electrode 100. FIG. 1 also illustrates portions of a secondary medical device, such as deep brain access device 102, and portions of a patient's brain in which electrode 100 and access device 102 are used. Electrode 100 includes a distal end 100A and a proximal end 100B. Proximal end 100B emerges from under a skin flap of the patient into which it has been inserted. Access device 102 includes, among other things, a base 104 access plate or ring secured concentrically around and/or in a burr hole 106 in the skull. Base 104 provides an access opening that is approximately the same diameter as a standard burr hole. Electrode 100 extends through burr hole 106 into a target location 108 in the brain, and is held in place by stabilizer 110. Access device 102 also includes a substantially rigid cap 112 that covers burr hole 106, stabilizer 110, and base plate 104, and is overlaid by a tapered low profile flexible (e.g., silicone or other elastomer) conformal cap 114 to soften the profile of the implanted apparatuses under the patient's scalp to more closely match the skull surface 116.

A suitable hole in conformal cap 114 and/or the overlying skin flap permits any upturned proximal portion 100B of electrode 100 to be exposed outside the skin flap, if desired. In this example, conformal cap 114 includes an engaging lip that mates with a lip of cap 112 or base 104. This holds conformal cap 114 in place.

In one example, portions of access device 102 allow attachment by other apparatuses during targeting/alignment, positioning, and/or acutely or chronically securing the implanted instrument. Although designed for use with a trajectory alignment system, stabilizer 110 can be used alone to stabilize catheters, needles, and drug and biological agent delivery instruments, as well as electrodes used for any purpose (e.g., electrical mapping, stimulation, or ablation) that have been placed using alternate targeting and placement methods and systems.

Figure 2:
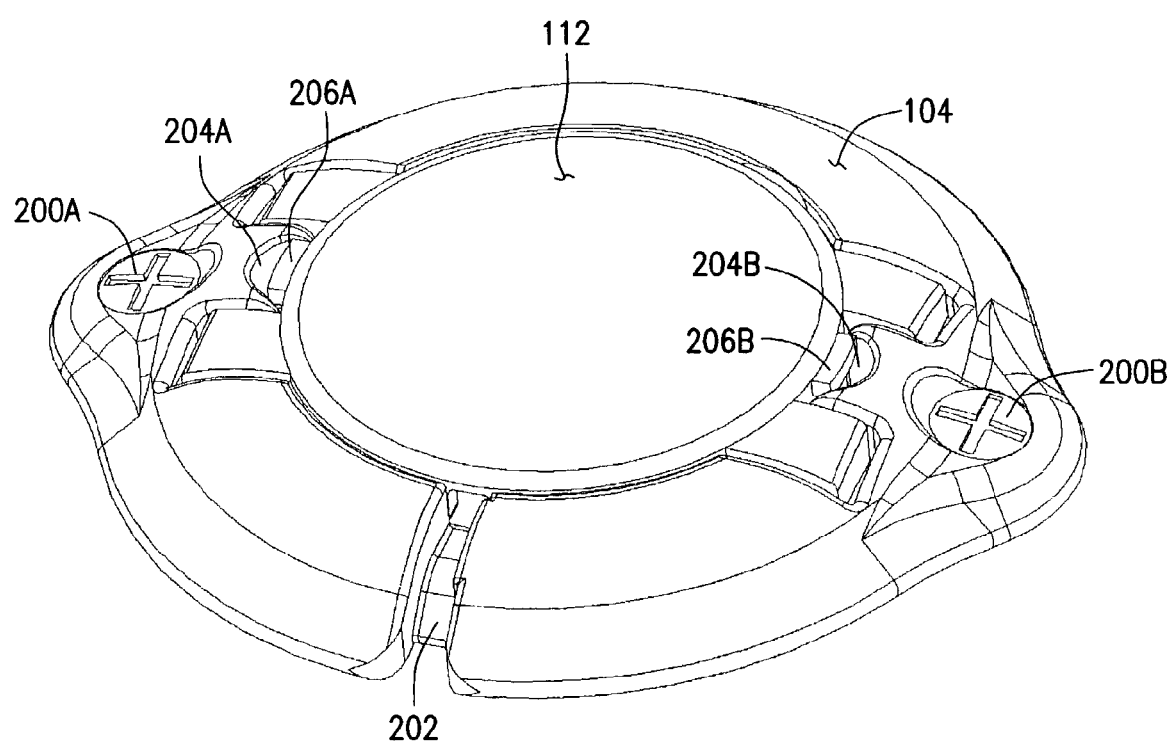
FIG. 2 is a perspective view example of a base and a cap.

FIG. 2 is a perspective view of an example base 104. In this example, base 104 is attached to the patient's skull by any suitable fastening device, such as bone screws 200A and 200B. Alternatively, base 104 is secured by threads that screw into burr hole 106. Other examples of attachment to the skull or other portions of the patient's body include adhesive, suction and other techniques. Base 104 includes one or more grooves 202 for receiving the proximal end 100B of electrode 100, or other flexible instrument, which is laterally bent into groove 202 for conformally exiting base 104, so that proximal end 100B of electrode 100 lies generally parallel to the skull surface 116. Proximal end 100B of electrode 100 extends along skull surface 116 for a clinically appropriate distance. Cap 112 covers portions of burr hole 106, and the assembly of base 104 and electrode 100. In this example, base 104 includes recesses 204A–B, such as for receiving respective pry lip extensions 206A–B of cap 112.

Figure 3:
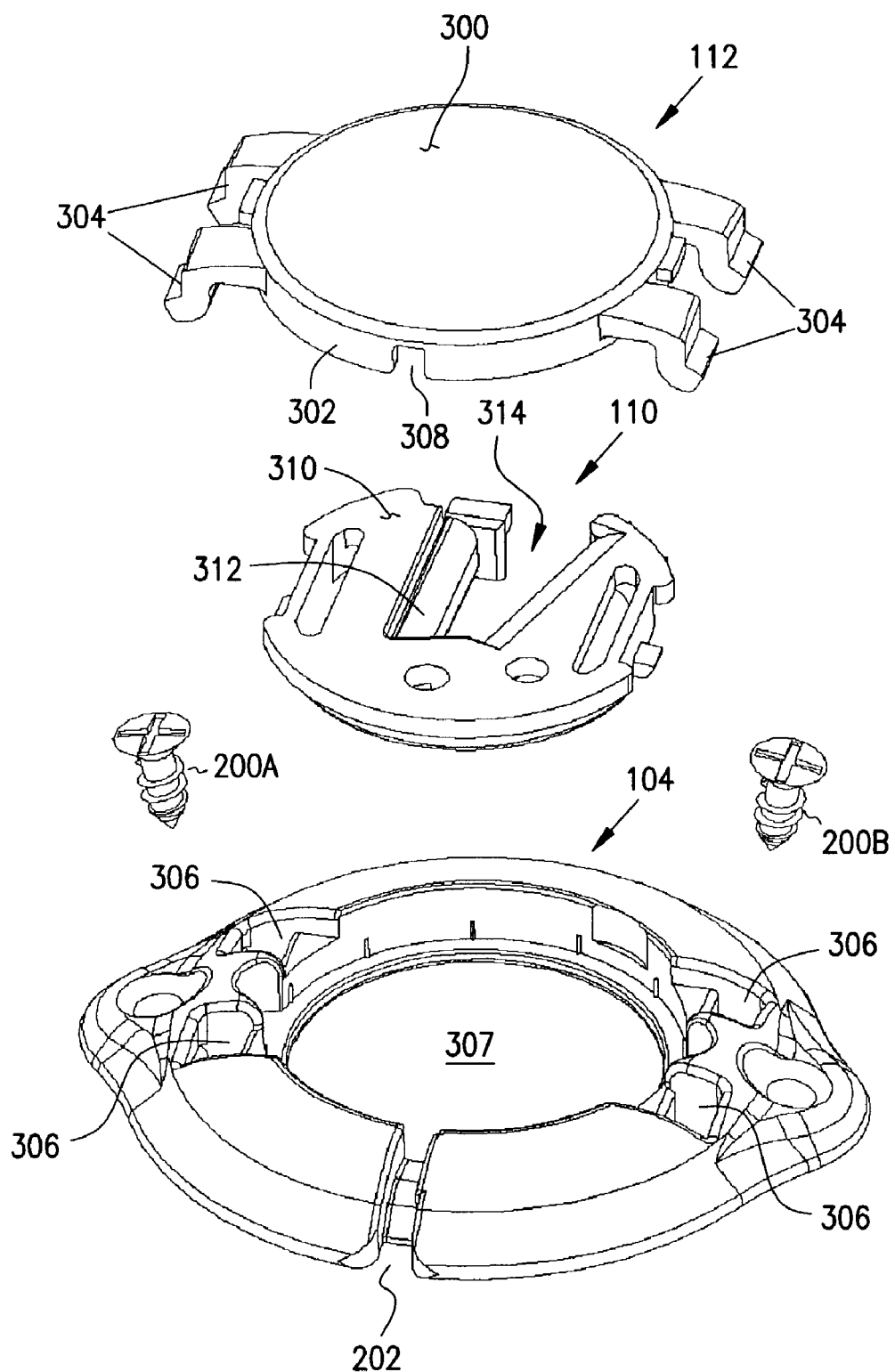
FIG. 3 is an exploded perspective view example of an assembly of a base, a stabilizer, and a cap.

FIG. 3 is an exploded view illustrating an example of an assembly of base 104, stabilizer 110, and cap 112. Cap 112 includes a relatively larger top 300 and a relatively smaller, generally cylindrical base 302. Cap 112 includes male finger or female receptacle snap-fits 304 (or other attachment device(s)) that are coupled to respective mating female receptacle or male finger snap-fits 306 of base 104 so that, when assembled, cap 112 is coupled to base 104, within its center opening 307, and covers stabilizer 110. The cylindrical base portion 302 of cap 112 includes at least one opening 308 permitting electrode 100 to exit base 104 via groove 202.

In the example of FIG. 3, stabilizer 110 includes a disk 310 coupled to a cam 312. Cam 312 rotates, with respect to disk 310, about an axis perpendicular to the plane of disk 310, to create and substantially close opening 314 in which electrode 100 is either passed freely (when open) or clamped (when closed) Thus, cam 312 is understood to include any form of clamping device. FIG. 3 illustrates cam 312 in its open position. Stabilizer 110 also includes snap-fits or other fastening features for coupling it to base 104. In the example of FIG. 3, stabilizer 110 can be snapped into base 104 in any rotational orientation. That is, the user can rotate stabilizer 110 a full 360 degrees to choose a specific rotational orientation with respect to base 104, and then snap stabilizer 110 into base 104 at that orientation. Moreover, elongate opening 314 extends radially from the center of the disk-like stabilizer 110 to its outer circumference. Along with the full rotational coupling capability of stabilizer 110, this allows an instrument, such as electrode 100, to be clamped within opening 314 in any location over the full area of opening 307 in base 104. This provides additional precision in placing the electrode 100 or other instrument.

Figure 4:
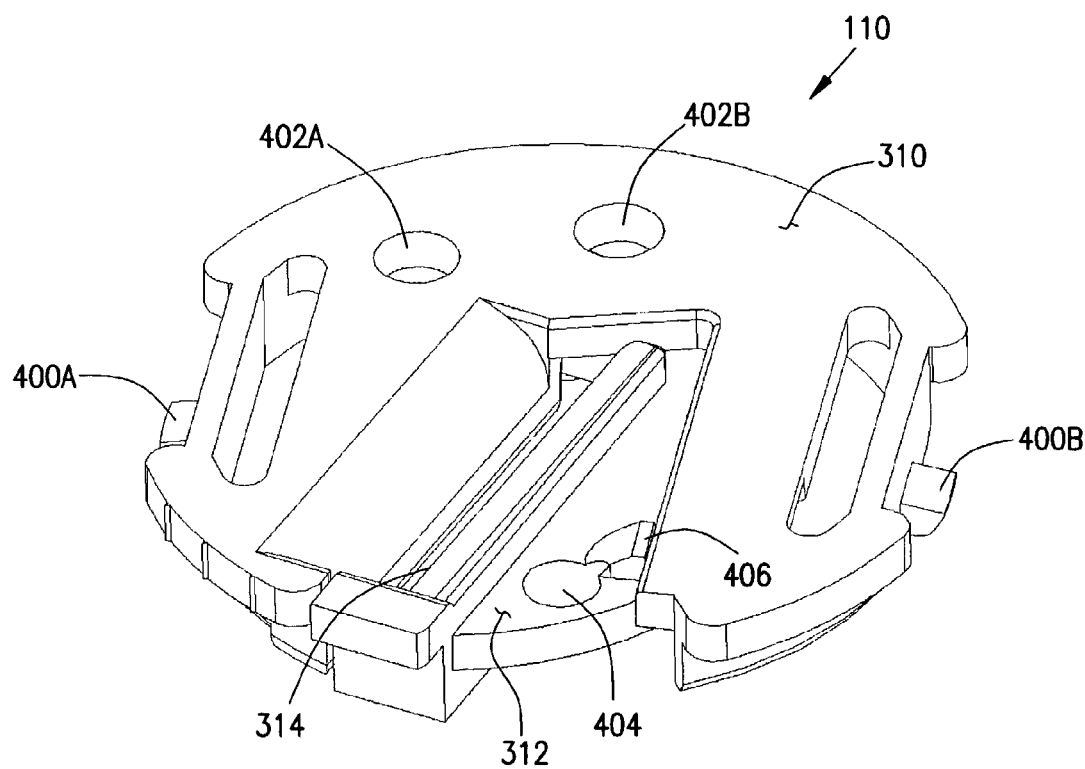
FIG. 4 is a perspective view example of a stabilizer.

FIG. 4 is a perspective view illustrating a closer view of stabilizer 110 in which cam 312 is in a closed position. FIG. 4 also illustrates coupling features 400A–B for coupling stabilizer 110 to base 104. In this example, one or more recesses 402A–B, or other engaging features, is provided. By using a tool that engages at least one of recesses 402A–B, stabilizer 110 can be placed into base 104 and snap-coupled thereto. Cam 312 also includes one or more recess 404, or other engaging feature. By using a tool that engages recess 404, cam 312 can be moved between open and substantially closed positions. In this example, cam 312 also includes a catch 406 that prevents unwanted accidental movement of cam 312 into the open position when cam 312 is intended to be in the closed position to secure electrode 100 or other medical instrument. In this manner, cam 312 locks into the closed position, and is opened by pressing down on a tool engaging recess 404. This allows catch 406 to slide under disk 310.

Figure 5:
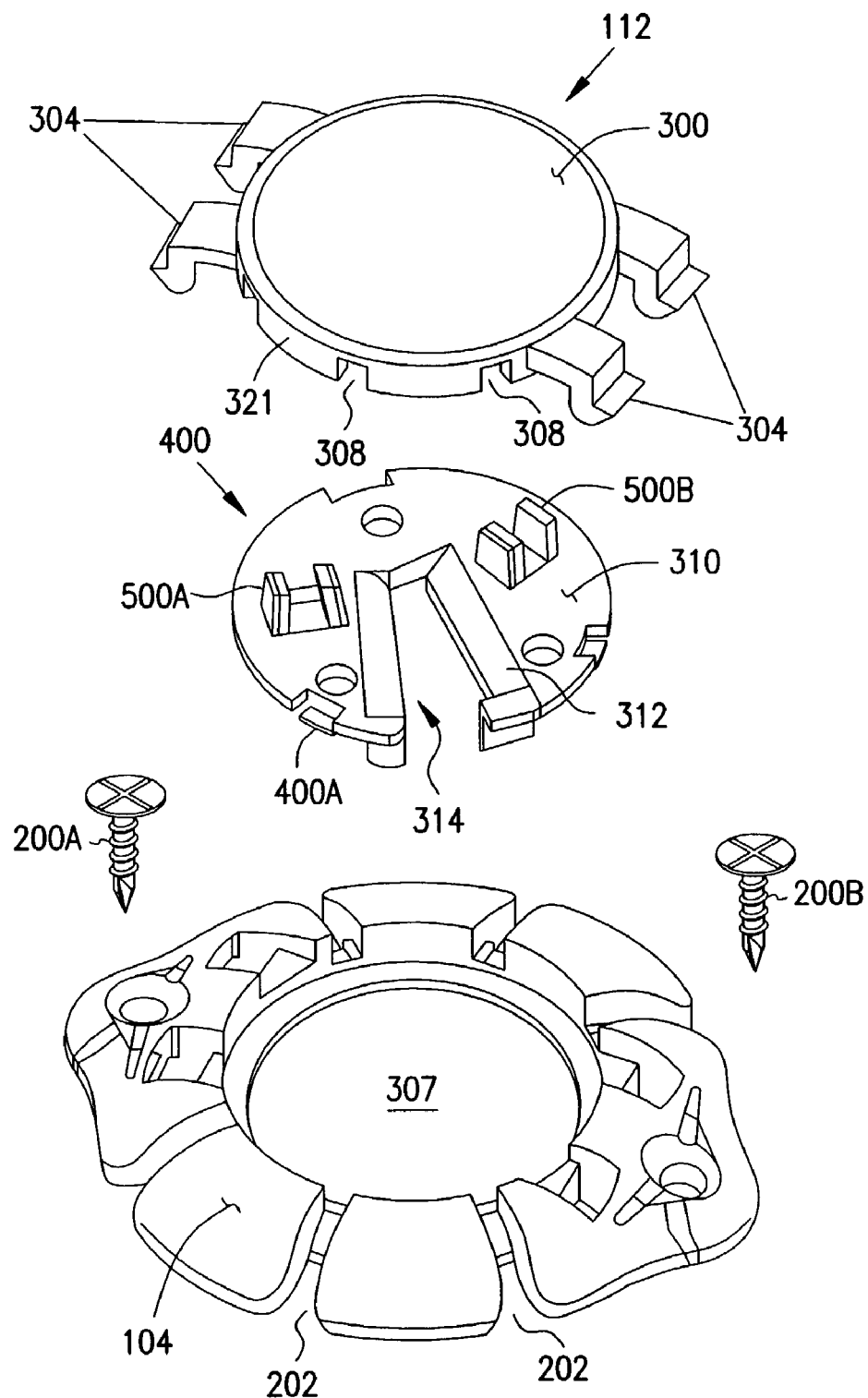
FIG. 5 is an exploded perspective view example of a base, a stabilizer, and a cap.

FIG. 5 is an exploded view of an alternate embodiment in which stabilizer 110 includes strain relief features 500A–B, either of which may be used to secure a small amount of slack in electrode 100 or other instrument. Also in this example, a plurality of grooves 202 in base 104, and a corresponding plurality of grooves 308 in cap 112, allows electrode 100 to laterally exit base 104.

FIG. 6 provides two perspective views of an example base positioner 600 device for centering base 104 around burr hole 106 (of known diameter) in the skull. A distal portion 602 of positioner 600 is appropriately sized to be received into center opening 307 of base 104 and further into burr hole 106. This centers base 104 concentrically around burr hole 106. Bone screws 200A–B are temporarily captured within openings in extension wings 604A–B of positioner 600, such that bone screws 200A–B are aligned to corresponding openings in base 104. Bone screws 200A–B are then loosely secured to the patient's skull, such that base 104 is properly positioned and centered around burr hole 106. Wings 604A–B are scored or otherwise constructed so as to separate when bone screws 200A–B are more securely tightened, thereby releasing bone screws 200A–B so that they can fasten base 104 to the patient's skull. Positioner 600 is then removed, such as by snapping it out of base 104, leaving base 104 securely fastened in the proper position with respect to burr hole 106.

Figure 7:
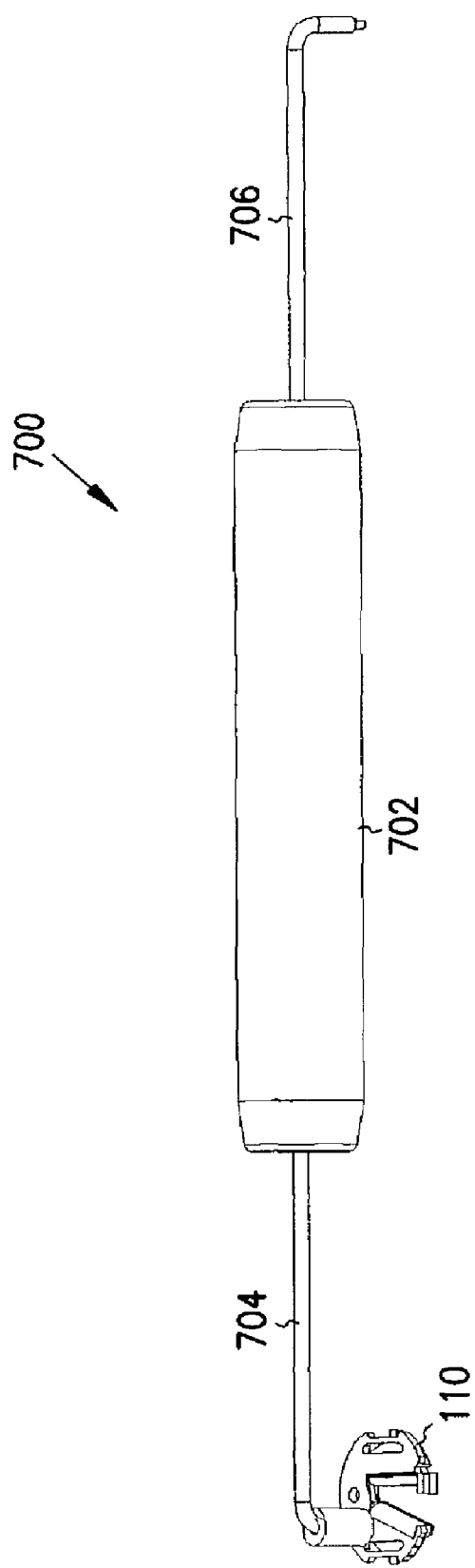
FIG. 7 is a perspective view example of a tool for placing the stabilizer, securing the introduced instrument, and removing the cap.

FIG. 7 is a perspective view of an example of a tool 700 for performing procedures with respect to, among other things, base 104, cap 112, and/or stabilizer 110. In this example, tool 700 includes a handle 702, a first engaging arm 704, and a second engaging arm 706. The end of arm 704 is appropriately sized to engage one of recesses 402A–B of disk 310 of stabilizer 110 for placing stabilizer 110 into base 104. The end of arm 706 is appropriately sized to engage recess 404 in cam 312 for moving cam 312 between its open and closed positions. In this example, at least one of ends 704 and 706 is appropriately sized for being inserted into one of recesses 204A–B (see FIG. 2) of base 104, and under one of corresponding extensions 206A–B for prying cap 112 away from base 104.

Figure 8:
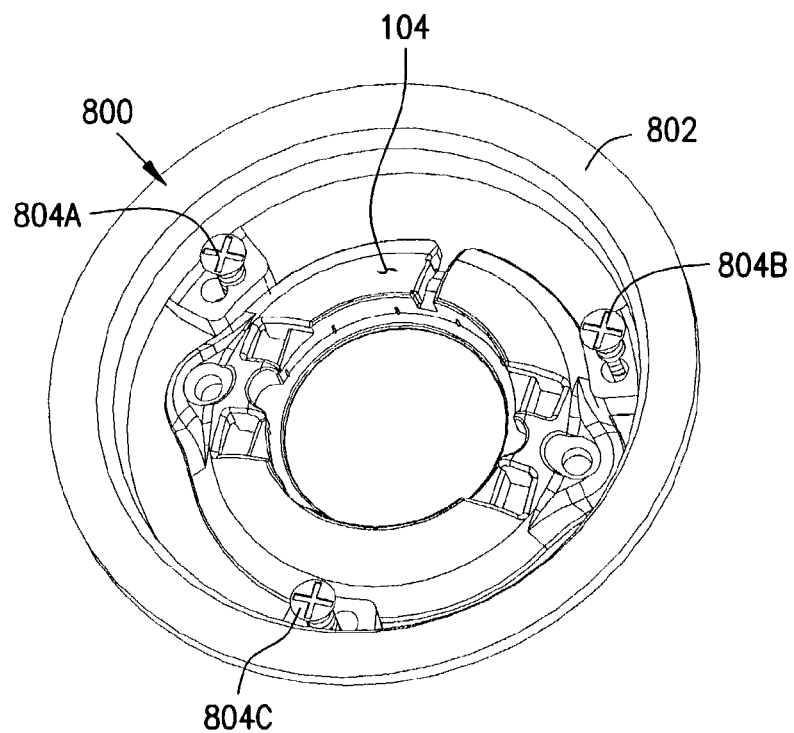
FIG. 8 is a perspective view example of an instrument-securing base and a equipment-supporting base.

FIG. 8 is a perspective view of an example of a different base, such as support base 800. In this example, support base 800 provides a ring-like or any other (e.g., cylindrical) suitable platform 802 for supporting other surgical equipment, such as for targeting/alignment of the trajectory of the instrument being introduced, and/or for introducing the instrument after such proper alignment is obtained. In this example, the equipment support base 800 is separate from instrument securing base 104, however, these two bases could alternatively be integrally formed or otherwise joined. In the example of FIG. 8, however, support base 800 is secured directly to the patient's skull over and around securing base 104, using bone screws 804A–C through legs extending downward from platform 802, by using any other appropriate affixation technique.

Figure 9:
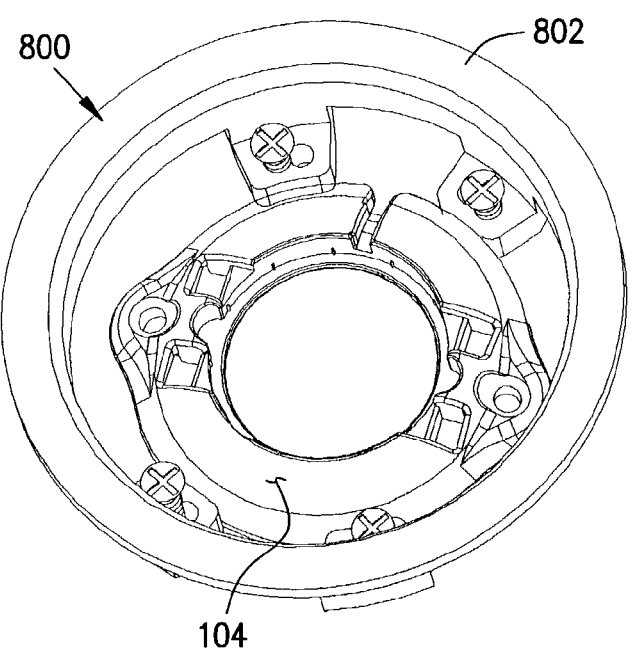
FIG. 9 is another perspective view example of an instrument-securing base and an equipment-supporting base.

FIG. 9 is a perspective view of an alternate example of a base 800, secured directly to the patient's skull by four bone screws 804A–D through respective legs extending downward from platform 802. This four-legged example advantageously allows for a smaller incision (e.g., in the direction of the instrument exit slot of base 104) into the patient's skull than the three-legged example of FIG. 8. Because the legs in the example of FIG. 9 are closer together than the legs in the example of FIG. 8, the skin does not have to be laterally spread apart as far to allow placement of the example of FIG. 9. Such a reduced lateral skin-spreading in turn reduces the required length of the incision slit.

Figure 10:
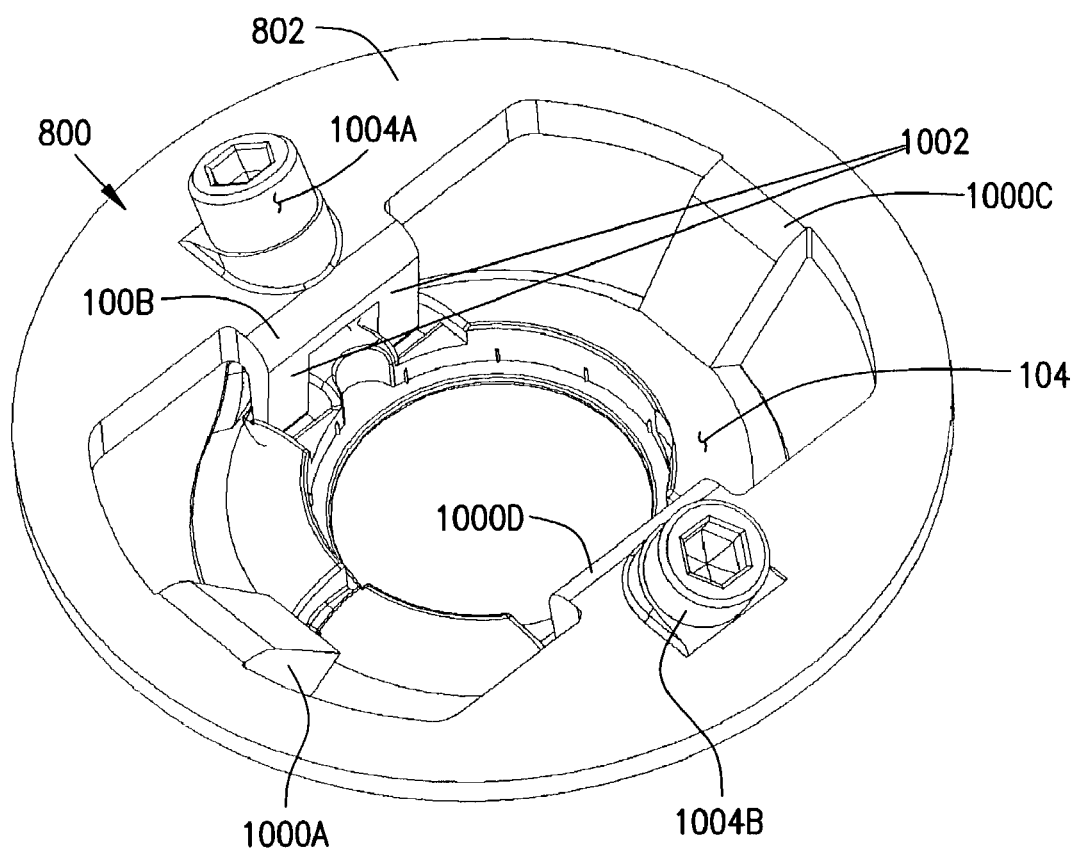
FIG. 10 is a further perspective view example of an instrument-securing base and an equipment-supporting base.

FIG. 10 is a perspective view of an alternate example of a support base 800. In this example, support base 800 is secured by any suitable means to instrument-securing base 104, which, in turn, is secured to the patient's skull, such as discussed above. In the example of FIG. 10, legs 1000A–D space platform 802 away from base 104. Each of legs 1000A–D includes one or more snap-fit features 1002 for engaging corresponding mating features on base 104. Tightening screws 1004A–B are each captured by a respective threaded portion of platform 802, and extend downward to press against base 104 when base 104 and platform 802 are snapped together. By adjusting screws 1004A–B, support base 800 is backed away from instrument-securing base 104 so that these two bases are more tightly coupled to each other. This provides added stability to platform 802.

Figure 11:
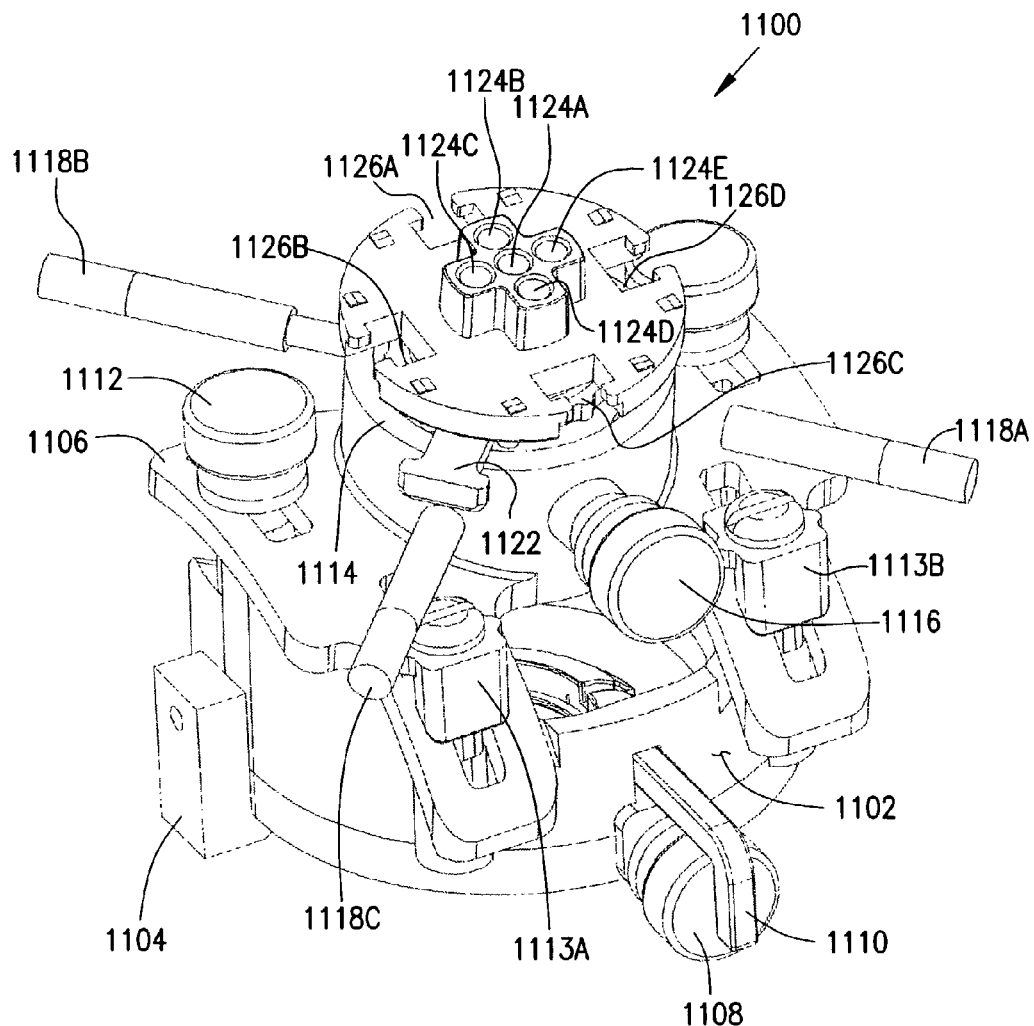
FIGS. 11 and 12 are perspective view examples of a tower-like instrument alignment and introduction guide assembly, also referred to as a deep brain access device.
Figure 12:
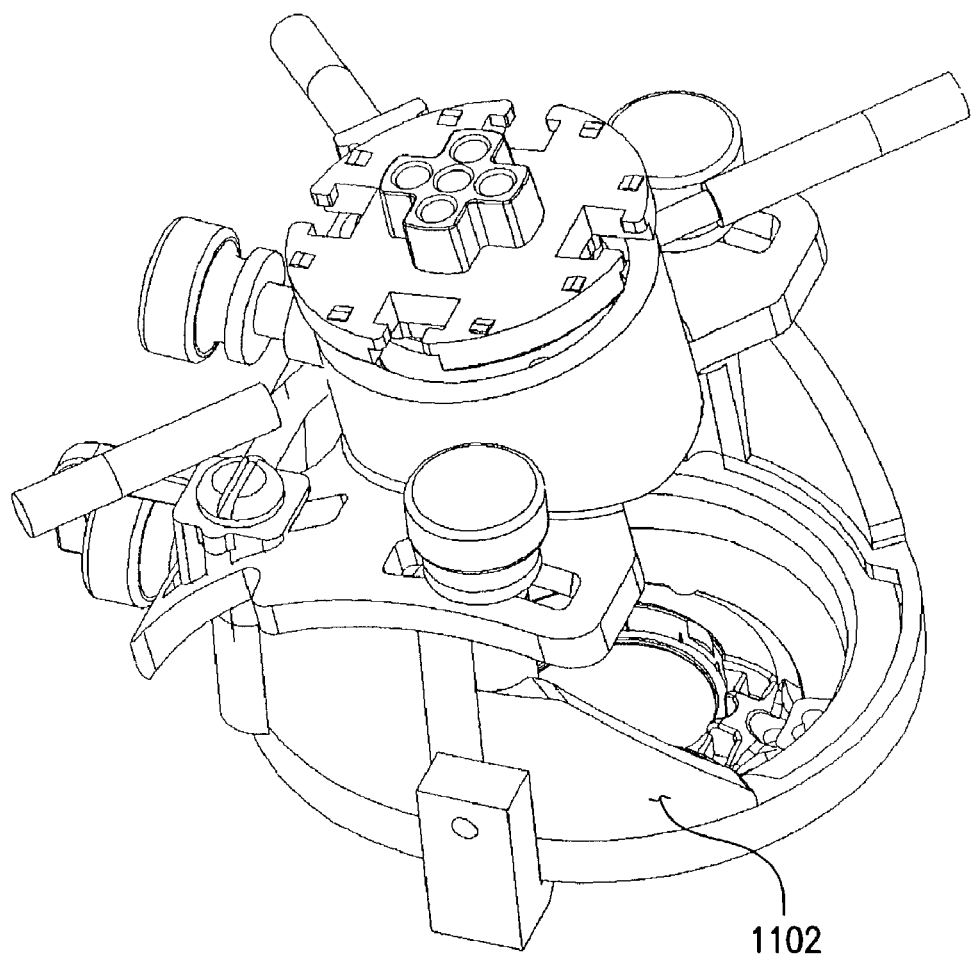

FIGS. 11 and 12 are perspective views of an example of a tower-like instrument alignment and introduction guide assembly, also referred to as a deep brain access device 1100. DBA device 1100 can also be regarded as including base 104, stabilizer 110, cap 112, and support base 800. A tower base 1102 of device 1100 snaps onto and rotates upon the ring-like or other platform 802 of FIGS. 8–10, such as by one or more snap-fitting side blocks 1104. Side blocks 1104 provide added stability to prevent tower base 1102 from rocking from side-to-side on platform ring 802. A curved saddle 1106 is coupled to and seated on a curved portion of tower base 1102, such as by at least one arcuate sliding joint, as illustrated. The curved portions of saddle 1106 and tower base 1102 can be tilted with respect to each other to alter a trajectory angle of an instrument being introduced, and can be secured to fix this aspect of the trajectory angle of the instrument.

An affixation mechanism, such as thumbscrew 1108, passes through an opening in tower base 1102 and engages a portion of platform 802 to prevent further rotation of tower base 1102 with respect to platform 802 once a desired rotational position has been obtained. In this example, a capturing device, such as L-shaped arm 1110, retains thumbscrew 1108 together with tower base 1102.

Another affixation mechanism, such as thumbscrew 1112, passes through a slotted opening (tilt slot) in saddle 1106 and engages a portion of tower base 1102 to prevent further riding of the curved portion of saddle 1106 along the curved portion of tower base 1102 once a desired trajectory angle has been obtained. This example also includes attachment fasteners 1113A–B passing through corresponding slots in saddle 1106 for additionally securing saddle 1106 to tower base 1102. Attachment fasteners 1113A–B include screws passing through respective retainer brackets, each of which includes a curved surface conforming to a curved surface of saddle 1106.

Also in this example, an interior portion of a socket 1114 on saddle 1106 provides a socket portion of a ball-and-socket joint. An affixation mechanism, such as thumbscrew 1116, passes through a threaded opening in socket 1114 to secure the position of a ball housed therein. Socket 1114 also includes fine-tuning thumbscrews 1118A–C, which pass through threaded openings in socket 1114 for further adjusting the exact position of a ball within socket 1114. Socket 1114 further carries a multilumen instrument guide insert assembly 1120. Multilumen insert 1120 includes a tapered sleeve that is releasably coupled, by release tab 1122 and associated structure(s), within a cylindrical opening through the spherical ball housed within socket 1114.

To release the multilumen insert 1120 from the ball, the tab 1122 is pressed inward toward the sleeve. This forces or wedges a portion of the release tab 1122 against a top portion of the ball and aids in releasing the multilumen insert 1120 from the ball. The top portion of multilumen insert 1120 provides a multilumen guide having a plurality of openings, such as the center opening 1124A and side openings 1124B–E; these openings are also referred to as lumens. Openings 1124B–E are spaced apart from center opening 1124A by a known predetermined distance. Therefore, if electrode 100 is inserted through center opening 1124A, and misses its target location 108 in the brain, it can be inserted into one of the side openings 1124B–E, without readjusting the trajectory, to reach a target at a known distance away from center opening 1124A in the plane of the multilumen insert 1120. In this example, multilumen insert 1120 also includes T-shaped receptacles or recesses 1126A–D for receiving further equipment, as discussed below. In one embodiment, multilumen insert 1120 includes one or more fiducial points (e.g., LEDs, reflective globes, or microcoils), such as for trajectory alignment in a frameless surgical navigation system or in an MRI environment.

Figure 13:
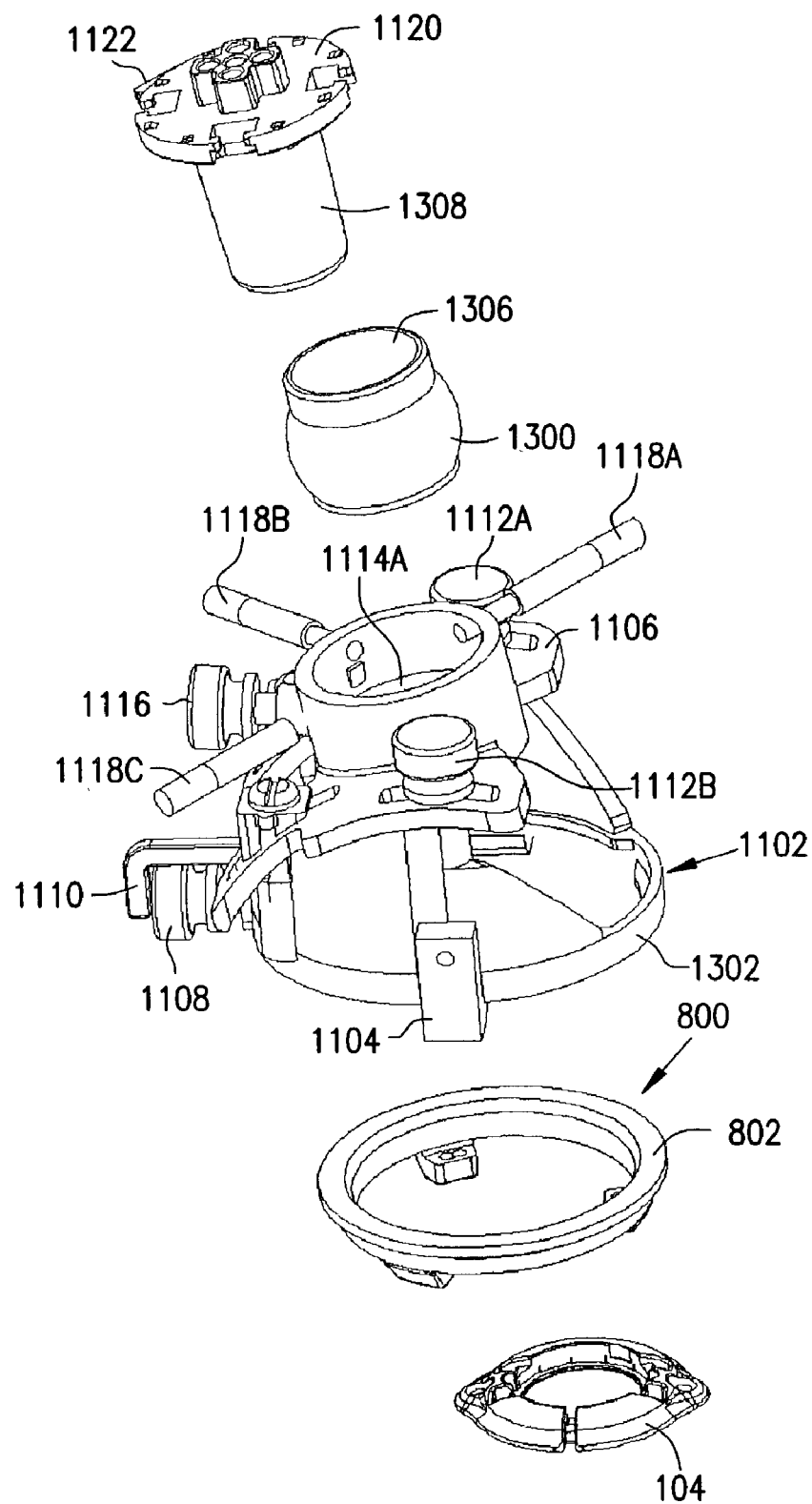
FIG. 13 is an exploded perspective view example of portions of a deep brain access device.

FIG. 13 is an exploded perspective view of an example of portions of deep brain access device 1100, including instrument-securing access base 104, support base 800, tower base 1102, saddle 1106, socket 1114A, ball 1300, multilumen insert 1120, and other associated components. As illustrated in FIG. 13, tower base 1102 includes a bottom or groove portion 1302 that engages platform 802, such as using hooked side blocks 1104, and allows tower base 1102 to rotate about the ring-like or other platform 802.

FIG. 13 also illustrates a cylindrical opening 1306 through ball 1300, which is seated in socket 1114A. Multilumen insert 1120 includes a tapered sleeve 1308 or barrel portion that fits snugly within opening 1306. Release 1122 includes a ring portion that fits over the exterior of sleeve 1308. To release multilumen insert 1120 from ball 1300, the tab portion of release 1122 is pressed inward toward sleeve 1308. This forces or wedges a portion of release 1122 against the top portion of ball 1300 and aids in releasing sleeve 1308 of multilumen insert 1120 from ball 1300. The tapered barrel provided by sleeve 1308 of multilumen insert 1120 includes, in one example, a closed end with openings corresponding to lumens 1124A–E of multilumen insert 1120.

Figure 14:
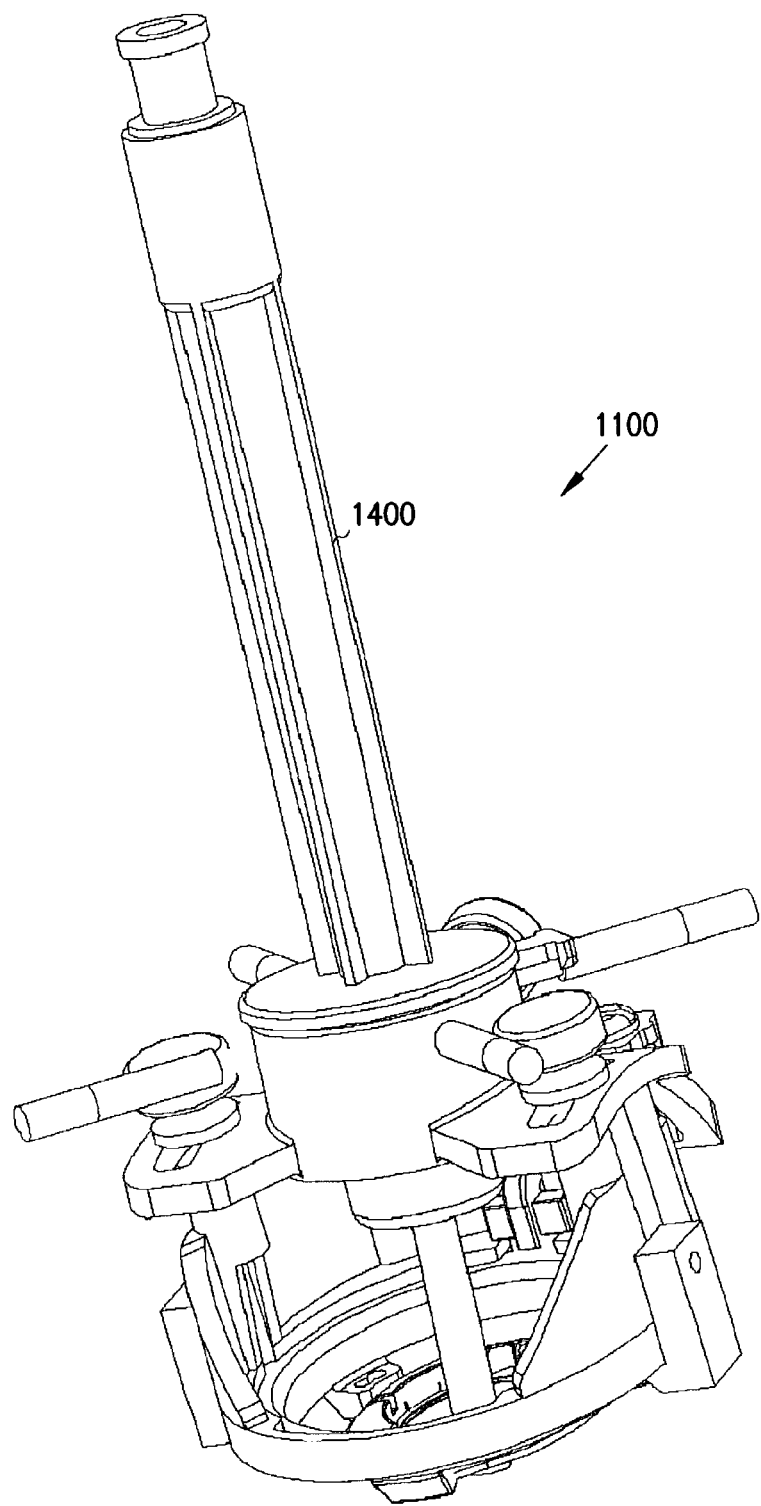
FIG. 14 is a perspective view example of adjusting an instrument trajectory using portions of a deep brain access device with MRI, CT, or another imaging modality.

FIG. 14 is a perspective view illustrating an example of adjusting an instrument trajectory using portions of deep brain access device 1100 with MRI, CT, PET, or another imaging modality. In FIG. 14, multilumen insert 1120 has been removed, and an imagable reference device, such as alignment stem 1400, has been inserted into the cylindrical passageway of ball 1300 in its place. In this example, alignment stem 1400 includes at least two fiducial points that are recognizable by the imaging modality. The various above-described positioning mechanisms of deep brain access device 1100 are adjusted to make the fiducial points collinear with the target location 108 in the brain. In one example, this may include adjusting the rotation of tower 1102 on platform 802, adjusting the tilt of saddle 1106 with respect to tower 1102, adjusting the spherical position of ball 1300 within socket 1114, and then fine tuning the exact position of ball 1300 using one or more of screws 1118A–C. The imaging modality includes a computer or other processor that provides a display indicating the relative alignment between the trajectory of alignment stem 1400 and target location 108. This display further indicates when the trajectory becomes collinear with target location 108 during the positioning process. The positioning mechanisms provide locking devices that are then locked in, and the alignment stem 1400 is replaced by multilumen insert 1120 for continuing the procedure of introducing electrode 100 or other instrument along this trajectory to target location 108 in the brain.

Figure 15:
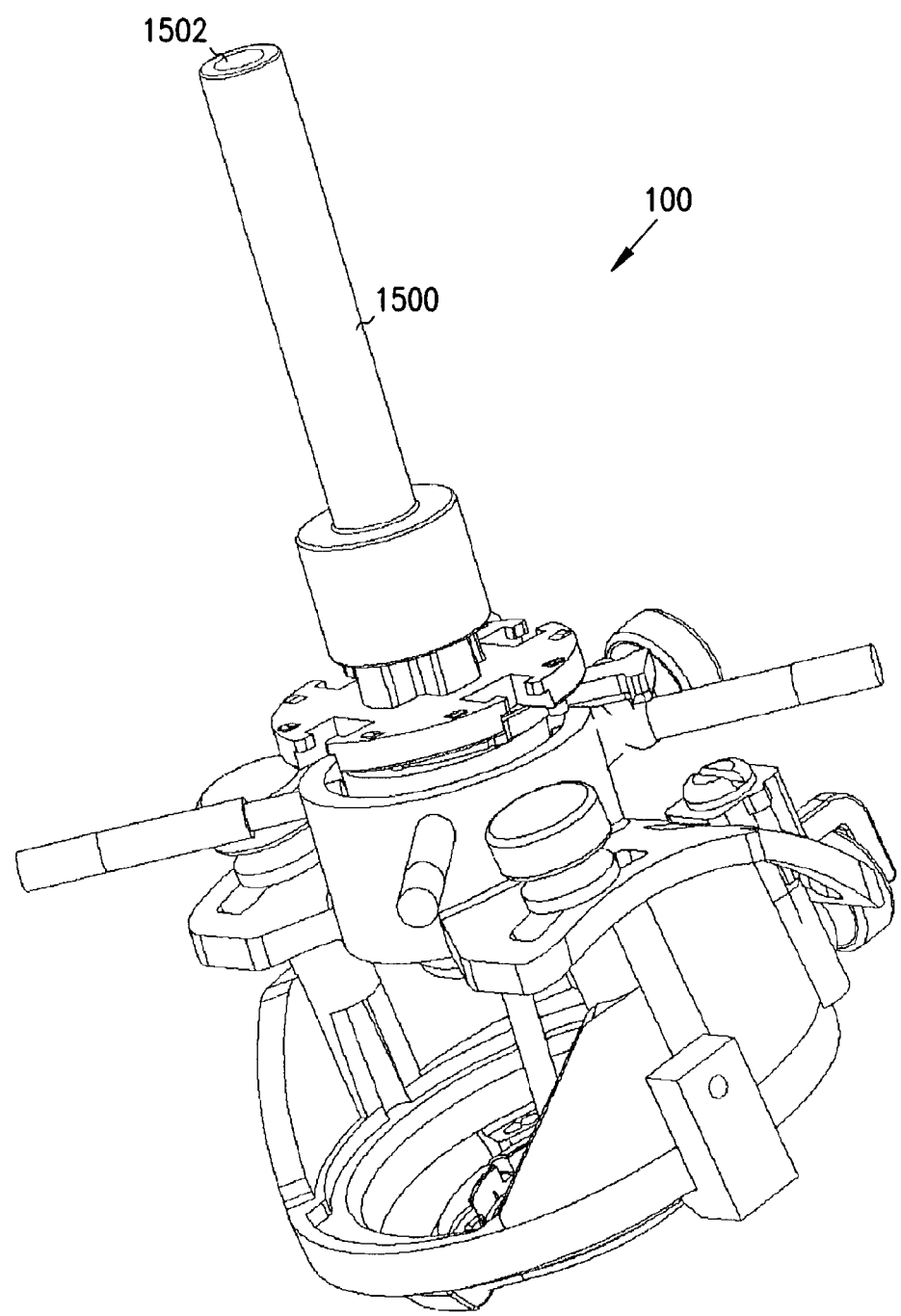
FIG. 15 is a perspective view example of adjusting an instrument trajectory using portions of a deep brain access device with a frameless surgical navigational system.

FIG. 15 is a perspective view illustrating an example of adjusting an instrument trajectory using portions of deep brain access device 1100 in conjunction with a frameless surgical navigational system. Examples of such systems use LEDs, light reflecting globes, or other spatially-separated fiducial markers to establish a desired instrument trajectory orientation. In the frameless example of FIG. 15, multilumen insert 1120 remains in place within the cylindrical passageway of ball 1300. Adapter 1500 is inserted into center lumen 1124A of multilumen insert 1120. In this example, adapter 1500 includes a center-bored seat 1502 that snugly receives a portion of frameless navigation reference device instrument. The frameless navigation reference instrument provides spatially-separated fiducial points that are recognized by the frameless imaging modality. These fiducial points are viewed, using the appropriate imaging modality, while the various positioning mechanisms of the deep brain access device are adjusted, to orient the instrument's trajectory toward the desired target location 108 in the brain, then locked in. The frameless navigation instrument is then removed from center-bored seat 1502 of adapter 1500. Adapter 1500 is then removed from center lumen 1124A of multilumen insert 1120 for continuing the procedure of introducing electrode 100 or other instrument along this trajectory to brain target location 108.

Figure 16:
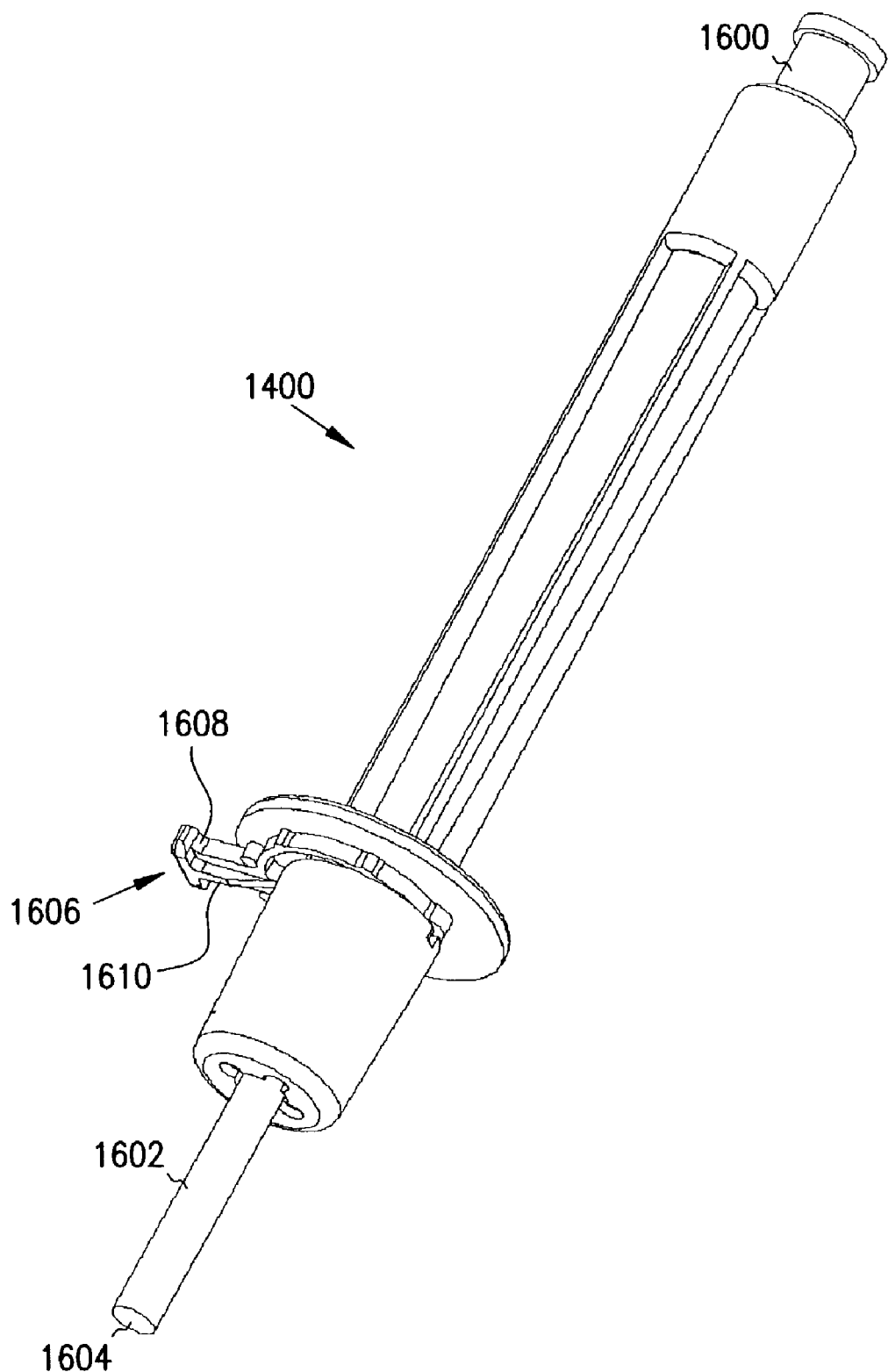
FIG. 16 is a perspective view example of an MRI-imagable alignment stem.

FIG. 16 is a perspective view illustrating an example of alignment stem 1400 when separated from deep brain access device 1100. In this example, alignment stem 1400 is filled with an imagable fluid provided through a one-way valve 1600 at a proximal end of alignment stem 1400. A distal end of alignment stem 1400 includes a protuberance or other extension 1602. In this example, extension 1602 is a thin cylindrical container having a distal tip 1604. Distal tip 1604 is located at the pivot point of ball 1300 when ball 1300 is seated in socket 1114 of saddle 1106. In this example, imagable fiducial points are provided at proximal valve 1600 and distal tip 1604. The trajectory is established by adjusting the various positioning mechanisms of deep brain access device 1100 so that these imagable fiducial points are collinear with target location 108 in the brain. In one example, the exact position of target location 108 is obtained using real-time imaging of the brain while the positioning mechanisms of deep brain access device 1100 are being adjusted. In another example, preoperative brain images are used to determine the position of target location 108 while adjusting the various positioning mechanisms of deep brain access device 1100. FIG. 16 also illustrates a release mechanism 1606, which includes knob 1608 and ramp 1610. By imparting a force on knob 1608 toward ball 1300, ramp 1610 engages the top of ball 1300 to assist in releasing alignment stem 1400 from the cylindrical passageway of ball 1300. Then, multilumen insert 1120 is reinserted into the cylindrical passageway of ball 1300, for introducing electrode 100 or other medical instrument(s) through lumen(s) 1124 of multilumen insert 1120.

Figure 17:
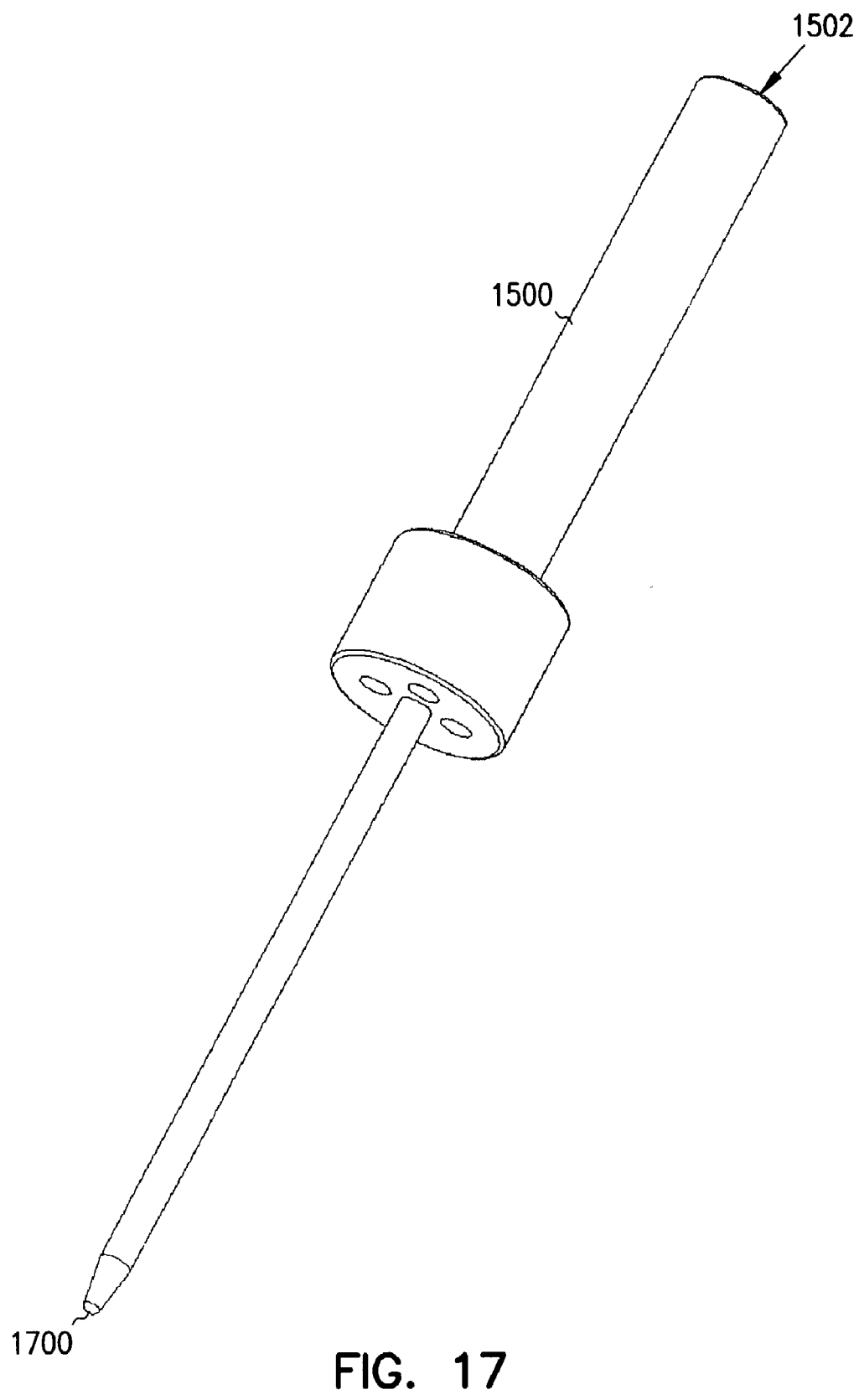
FIG. 17 is a perspective view example of an adapter for receiving a frameless surgical navigation instrument.

FIG. 17 is a perspective view illustrating an example of frameless adapter 1500 when separated from deep brain access device 1100. In this example, adapter 1500 includes stainless steel pin, having a distal tip 1700, that is appropriately sized for being inserted into center lumen 1124A of multilumen insert 1120. When fully inserted, distal tip 1700 is located the pivot point of ball 1300 when ball 1300 is seated in socket 1114 of saddle 1106. In this example, a frameless navigation instrument with frameless imagable fiducial points is inserted into center-bored seat 1502 at the proximal end of adapter 1500, or onto the outer portion of adapter 1500, or otherwise coupled to adapter 1500 by any other appropriate coupling technique.

Figure 18:
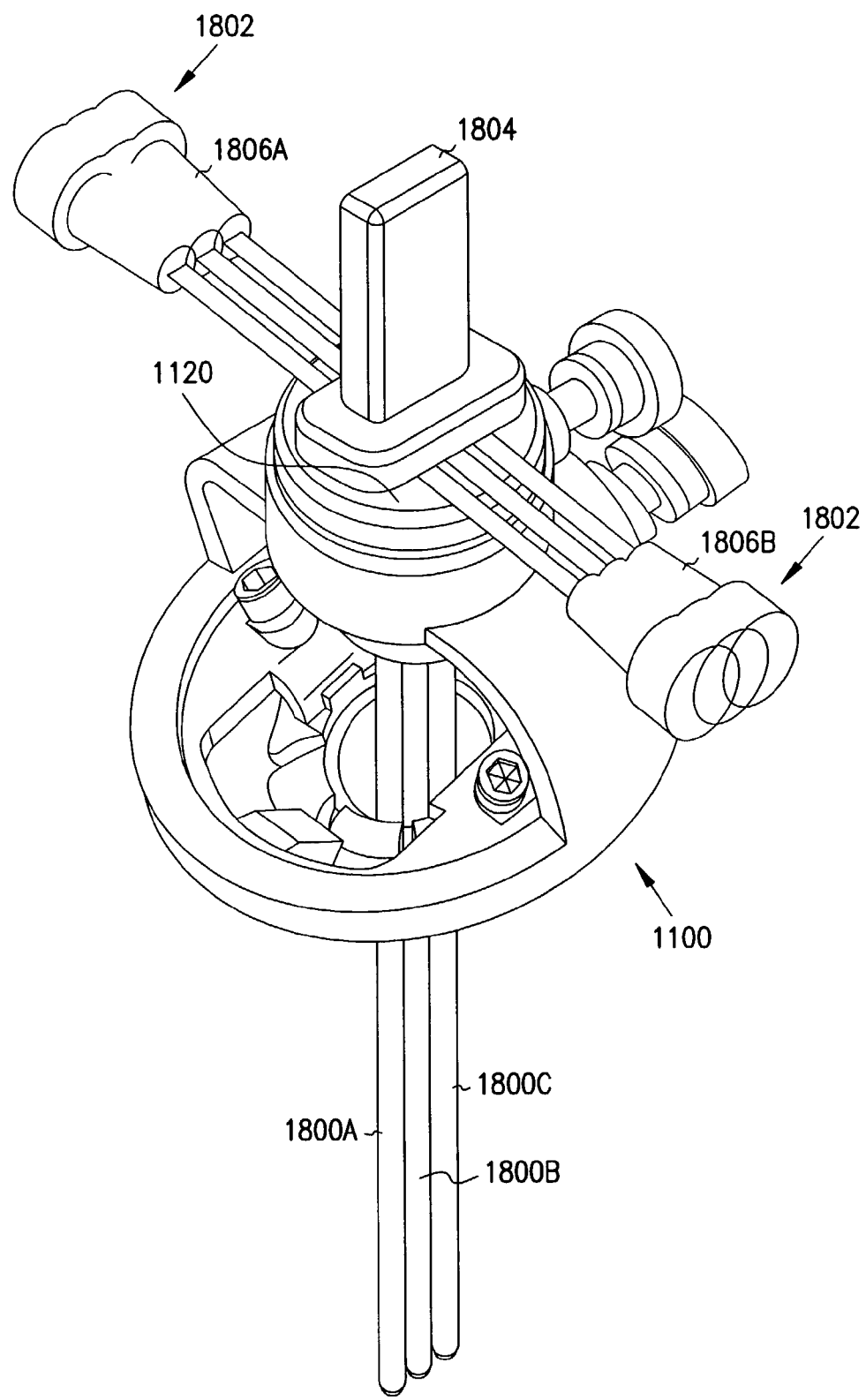
FIG. 18 is a perspective view example of a technique for introducing an instrument along the previously established trajectory using a peel-away sheath and stylet.

FIG. 18 is a perspective view illustrating an example of a technique for introducing an instrument along the previously established trajectory to target location 108 in the brain. In FIG. 18, multilumen insert 1120 is used to guide a distal end of a secondary medical instrument, such as an elongate lumenal catheter or peel-away sheath, for example, one of sheaths 1800A–C, toward target location 108. Before sheath 1800 is inserted into one of lumens 1124A–E of multilumen insert 1120, however, a stylet is inserted through a hollow center bore or lumen of sheath 1800. This prevents coring of brain tissue by the hollow center bore of sheath 1800 and, in one embodiment, provides additional rigidity for performing the insertion and obtaining an accurate path along the established trajectory toward target location 108.

The example of FIG. 18 illustrates a triple sheath assembly 1802, with linearly-arranged sheaths 1800A–C, appropriately spaced apart for being inserted into three linearly-arranged lumens 1124 of multilumen insert 1120. This example similarly illustrates a triple stylet assembly 1804 in which three linearly-arranged stylets are spaced apart for insertion in the linearly-arranged sheaths 1800A–C. This triple sheath/stylet illustration is merely an example. The exact number of sheaths 1800 and corresponding stylets being introduced ranges from a single sheath/stylet to the number of available lumens 1124 in multilumen insert 1120. After sheath assembly 1802 and stylet assembly 1804 has been guided approximately to target location 108, stylet assembly 1804 is removed and a guide bridge is secured to multilumen insert 1120 for guiding electrode 100 into the center bore of one of sheaths 1800A–C for positioning electrode 100 at target location 108. The sheaths 1800A–C are then removed by pulling apart handles 1806A–B. In the illustrated example, each sheath 1800 breaks into two pieces as it is being extracted.

Figure 19B:
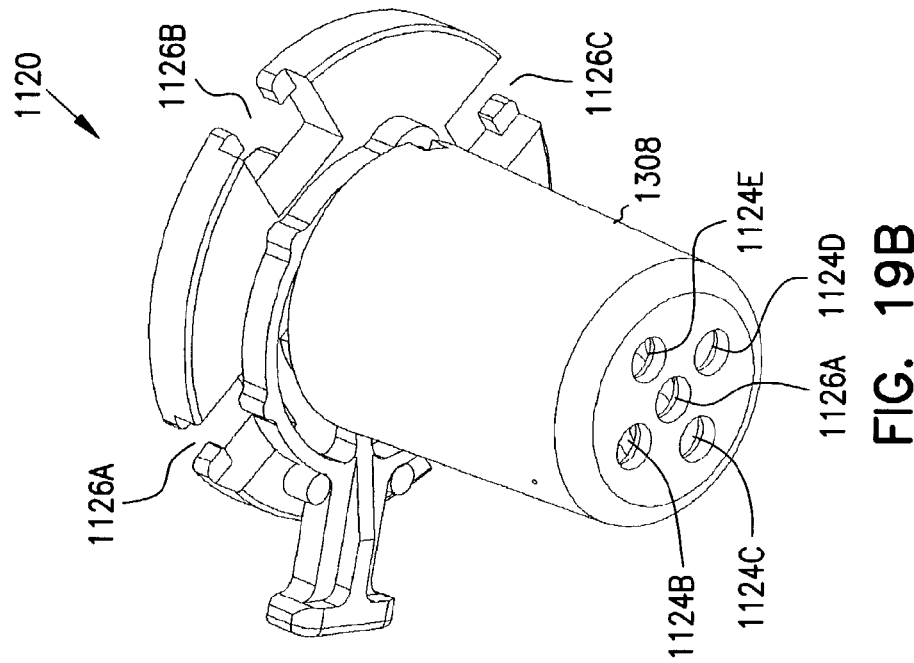
FIG. 19 provides two perspective view examples of a multilumen insert portion of a deep brain access device.
Figure 19A:
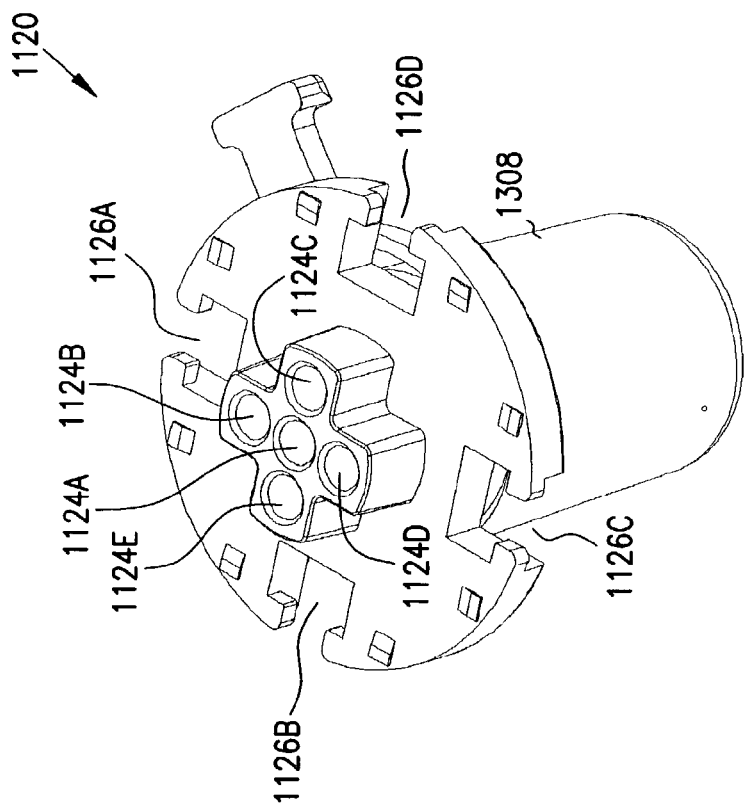

FIG. 19 provides two perspective views of an example of multilumen insert 1120, which includes the tapered barrel-like sleeve 1308 that is inserted into center hole 1306 of ball 1300. Lumens 1124A–E extend from the top of multilumen insert 1120 through the barrel sleeve 1308. As discussed above, side lumens 1124B–E are appropriately radially-spaced (e.g., 3 millimeters, center-to-center) from center lumen 1124A to provide capability for repositioning of electrode 100 by a known amount by simply removing electrode 100 from center lumen 1124A and reinserting it into a desired one of side lumens 1124B–E. FIG. 19 also illustrates receptacles 1126A–D, opposing pairs of which are used for receiving a guide bridge or other equipment desired to be mounted to the top of multilumen insert 1120.

Figure 20:
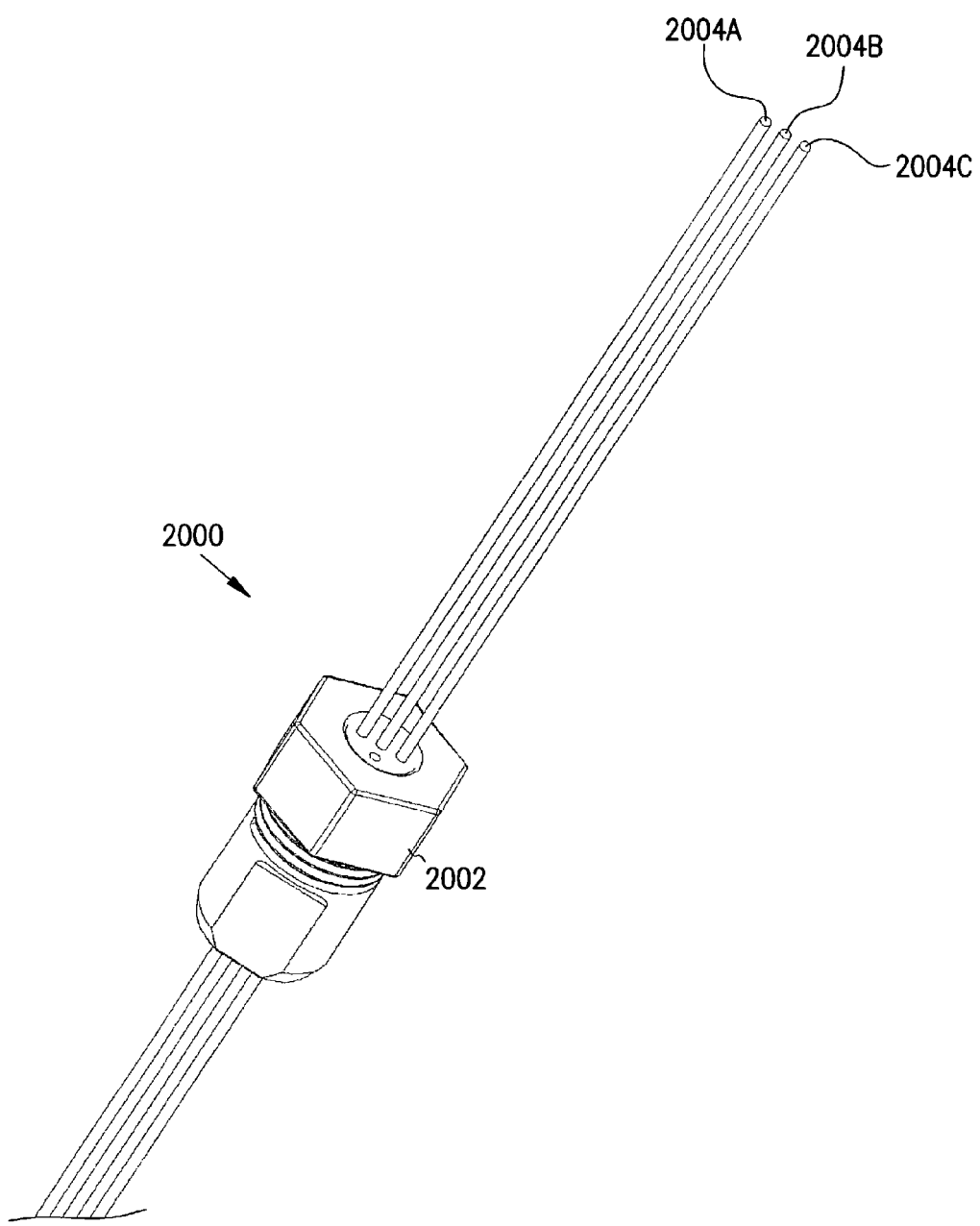
FIG. 20 is a perspective view example of a hub and stylets.

FIG. 20 is a perspective view illustrating an alternate example of a stylet assembly 2000, including a hub 2002 for uniting 1–5 stylets 2004A–C for insertion into corresponding peel-away or other sheaths inserted through corresponding lumens 1124 of multilumen insert 1120. In one embodiment, hub 2002 includes a Touhy-Borst adapter, or other suitable adapter for gripping stylets 2004A–C.

Figure 21:
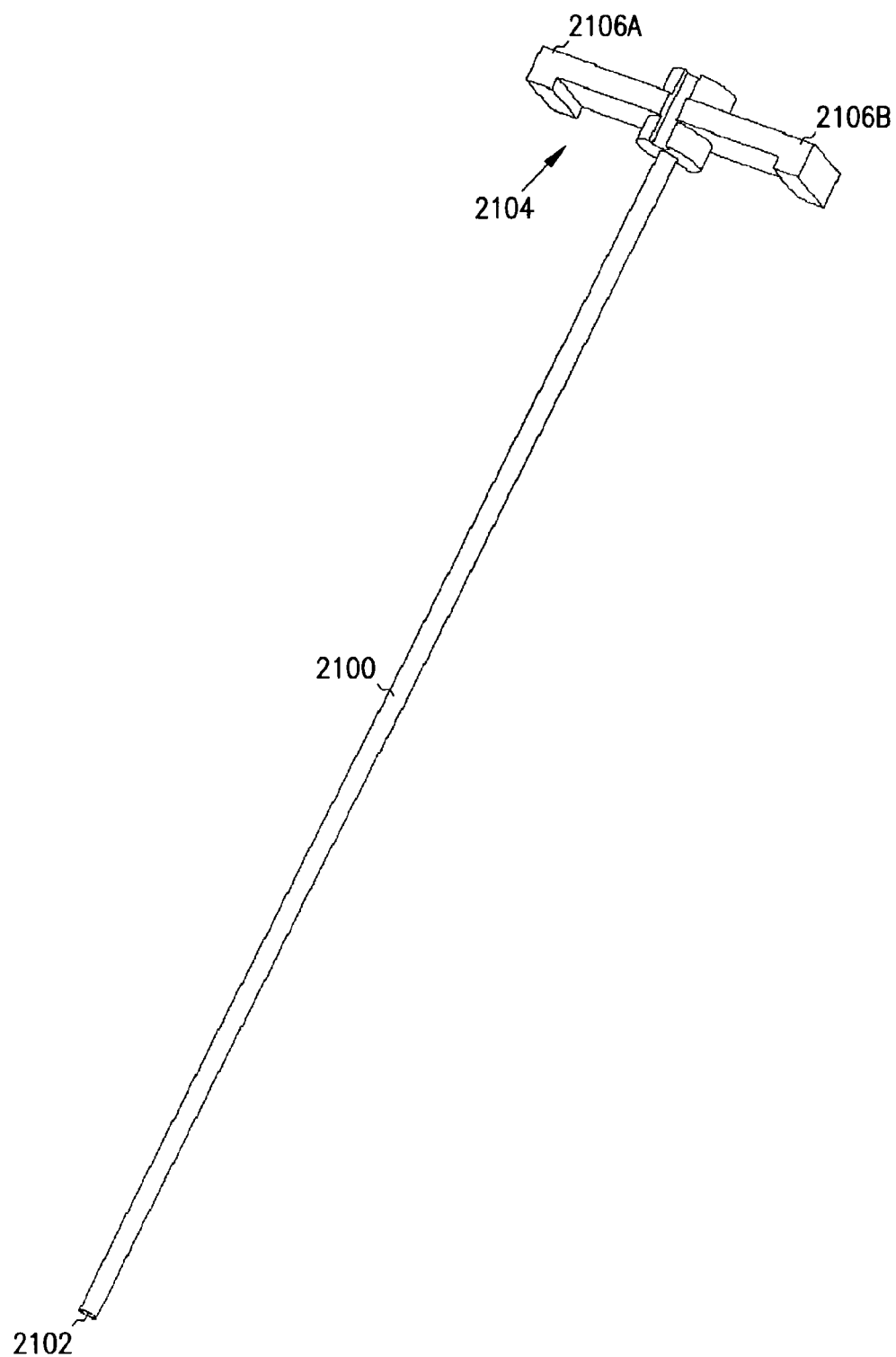
FIG. 21 is a perspective view example of a single peel-away sheath.

FIG. 21 is a perspective view illustrating an example of a single peel-away sheath 2100 including a distal tip 2102, a proximal end 2104, and a center bore or lumen extending therebetween. Handles 2106A–B are included at proximal end 2104. Sheath 2100 is peeled away and extracted by pulling apart handles 2106A–B.

Figure 22:
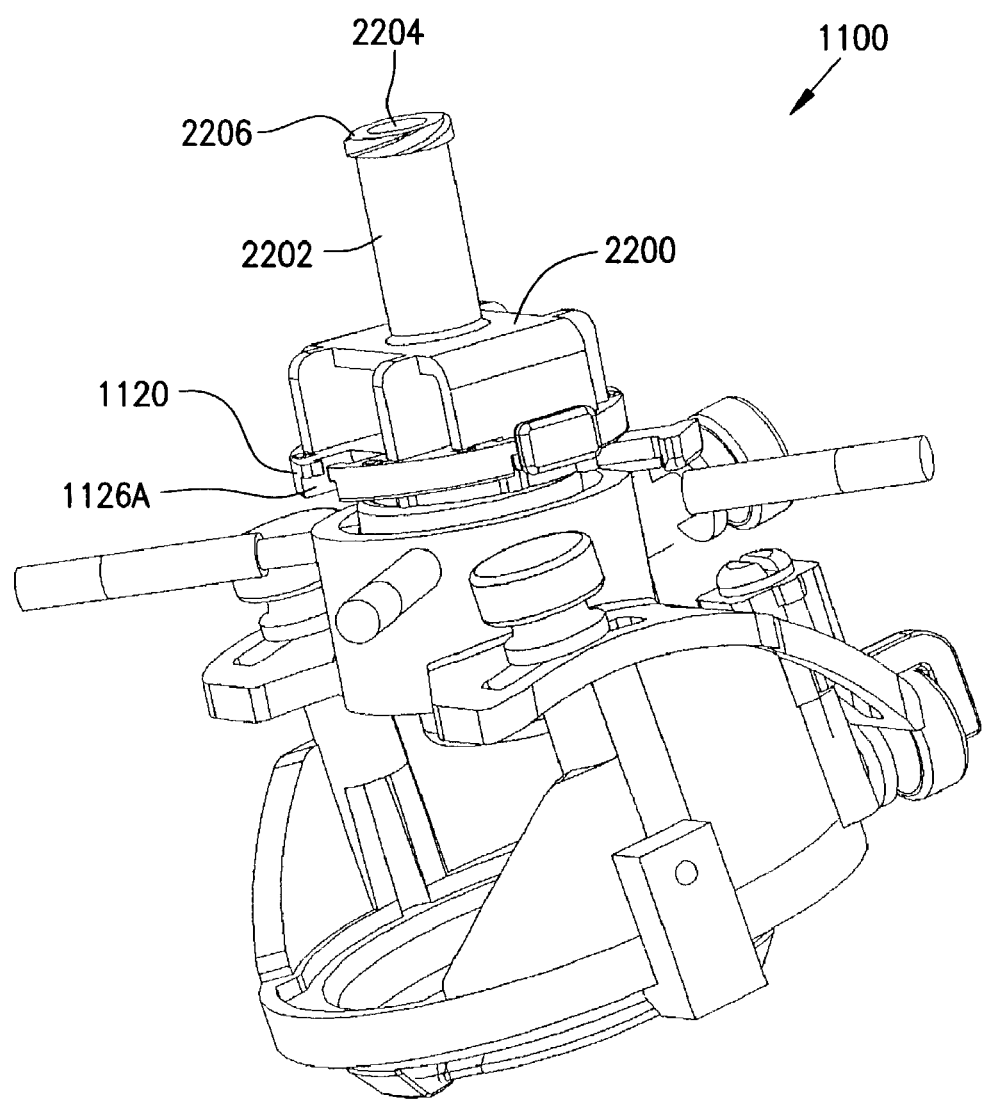
FIG. 22 is a perspective view example of a guide bridge mounted onto a multilumen insert of a deep brain access device.

FIG. 22 is a perspective view illustrating an example of a guide lumen selector, such as guide bridge 2200 having tabs or legs that are snap-mounted onto an opposing pair of receptacles 1126A–D of multilumen insert 1120. In this example, guide bridge 2200 includes a cylindrical guide tube 2202 extending upward from a base portion of guide bridge 2200. Guide tube 2202 includes a center bore hole 2204 for passing electrode 100 or other instrument therethrough. A proximal portion of guide tube 2202 includes a lip 2206 extending outward circumferentially around the perimeter of guide tube 2202. In one example, the center bore hole 2204 is tapered inward in a direction away from lip 2206. That is, an inner diameter of bore hole 2204 necks down so the instrument passed therethrough is automatically centered as it approaches the base portion of guide bridge 2200. In this example, guide bridge 2200 also assists in holding the sheath(s) in place as the electrode is being passed through a sheath to target location 108. The handle portions of the sheath do not pass through guide tube 2202, but instead, exit under the sides of guide bridge 2200. In one example, guide bridge 2200 includes a wedge-like ridge on its underside to assist in splitting the peel-away sheath.

Figure 24:
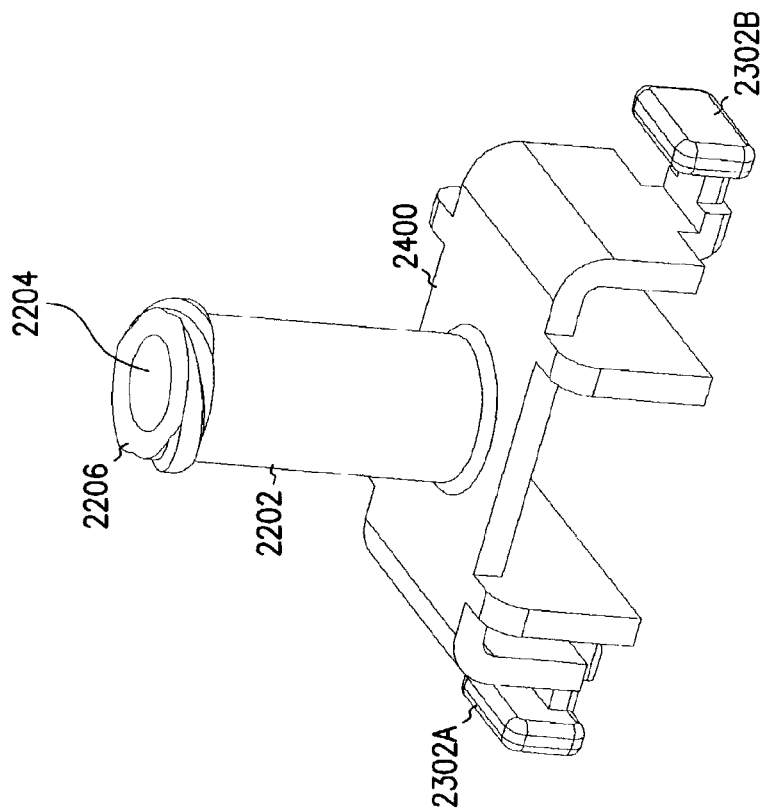
FIG. 24 is a perspective view example of a center guide bridge.
Figure 23:
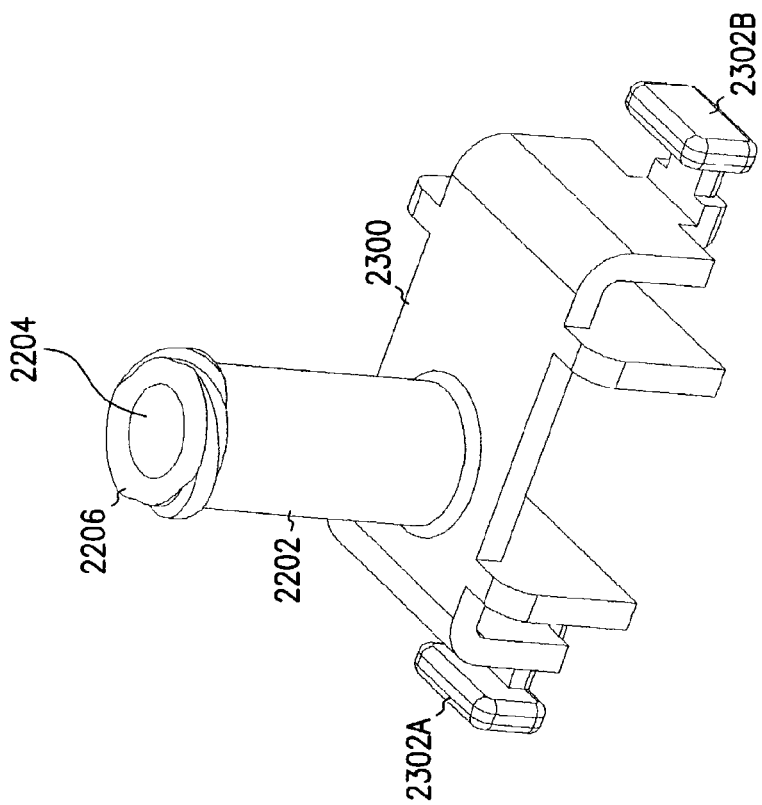
FIG. 23 is a perspective view example of an offset guide bridge.

FIGS. 23 and 24 are perspective views illustrating an offset guide bridge 2300 and a center guide bridge 2400, respectively. Lumens 1124A–E provide a primary guide device for electrode 100 or other instrument, and the selected one of offset guide bridge 2300 and center guide bridge 2400 provides a secondary guide device for electrode 100 or other instrument. Offset guide bridge 2300 is selected when the instrument being introduced is intended to pass through one of side lumens 1124B–E in multilumen insert 1120. In this example, guide tube 2202 is offset from the center of the base of offset guide bridge 2300, such that its center bore 2204 is aligned with one of side lumens 1124B–E of multilumen insert 1120. Alignment with the particular desired side lumen is obtained by appropriately rotating the orientation of offset guide bridge 2300 and snapping tabs 2302A–B into corresponding opposing pairs of receptacles 1126. By contrast, in center guide bridge 2400, guide tube 2202 is centered on the base portion of center guide bridge 2400, such that its center bore 2204 aligns with center lumen 1124A of multilumen insert 1120 when center guide bridge 2400 is snapped into opposing pairs of receptacles 1126 of multilumen insert 1120. In each of the examples of FIGS. 23 and 24, an outside portion of lip 2206 is threaded for engaging other equipment. Alternatively, other equipment may be mounted onto guide tube 2202 by using a compression fit to a threaded or unthreaded lip 2206.

Figure 25:
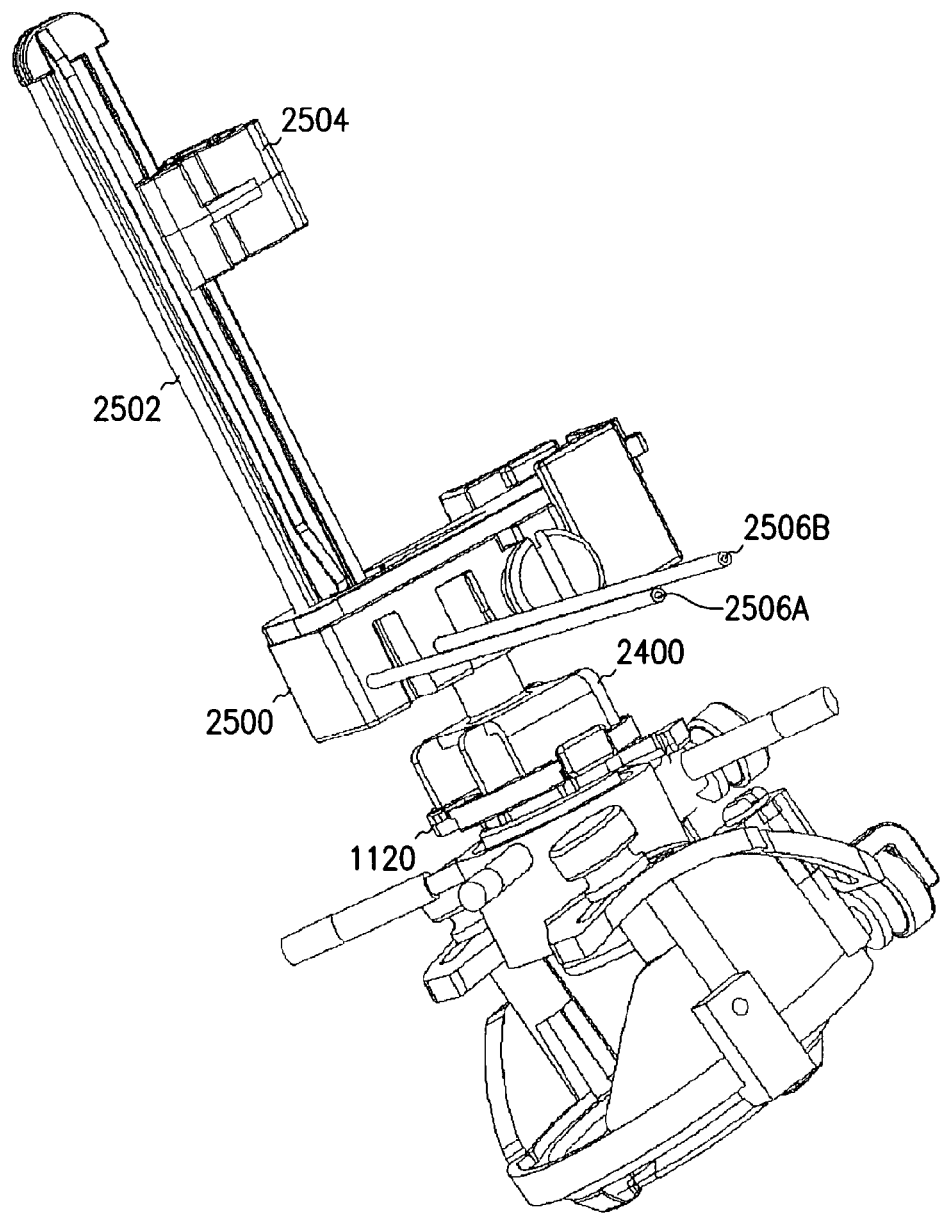
FIGS. 25 and 26 are perspective view examples, respectively, of a remote introducer mounted onto a deep brain access device.
Figure 26:
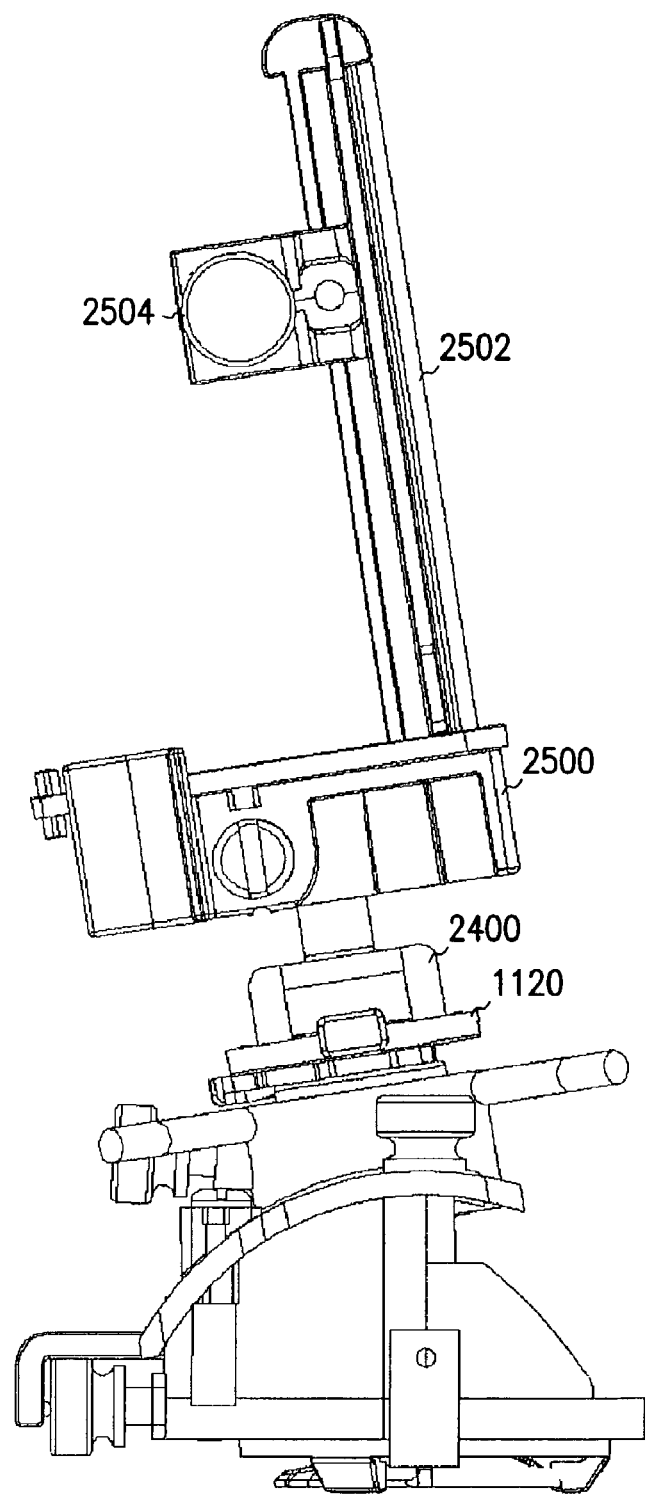

FIGS. 25 and 26 are perspective views of deep brain access device 1100, on which a center guide bridge 2400 is mounted to multilumen insert 1120. In these examples, an introducer 2500 mechanism is mounted onto guide tube 2202 using a compression fitting to lip 2206. Introducer 2500 includes a slide 2502 mechanism on which a sliding clamp 2504 rides toward and away from deep brain access device 1100 and, therefore, toward and away from burr hole 106 in the skull or other entry portal. Clamp 2504 holds the electrode 100 or other instrument being introduced. In one example, introducer 2500 is operated remotely by controls 2506A–B to slide clamp 2504 along slide 2502, and therefore, to introduce the instrument being held by clamp 2504 into and/or out of the brain along the predetermined trajectory in a controlled manner. One example of an appropriate remote introducer 2500 is the Fathom® Remote Introducer available from Image-Guided Neurologics, Inc. of Melbourne, Fla. U.S.A. Another example of an appropriate remote introducer 2500 is described in Skakoon et al. U.S. patent application Ser. No. 09/827,266, entitled "Medical Device Introducer," filed on Apr. 5, 2001 and assigned to the assignee of the present patent application, the disclosure of which is incorporated herein by reference in its entirety.

Figure 27:
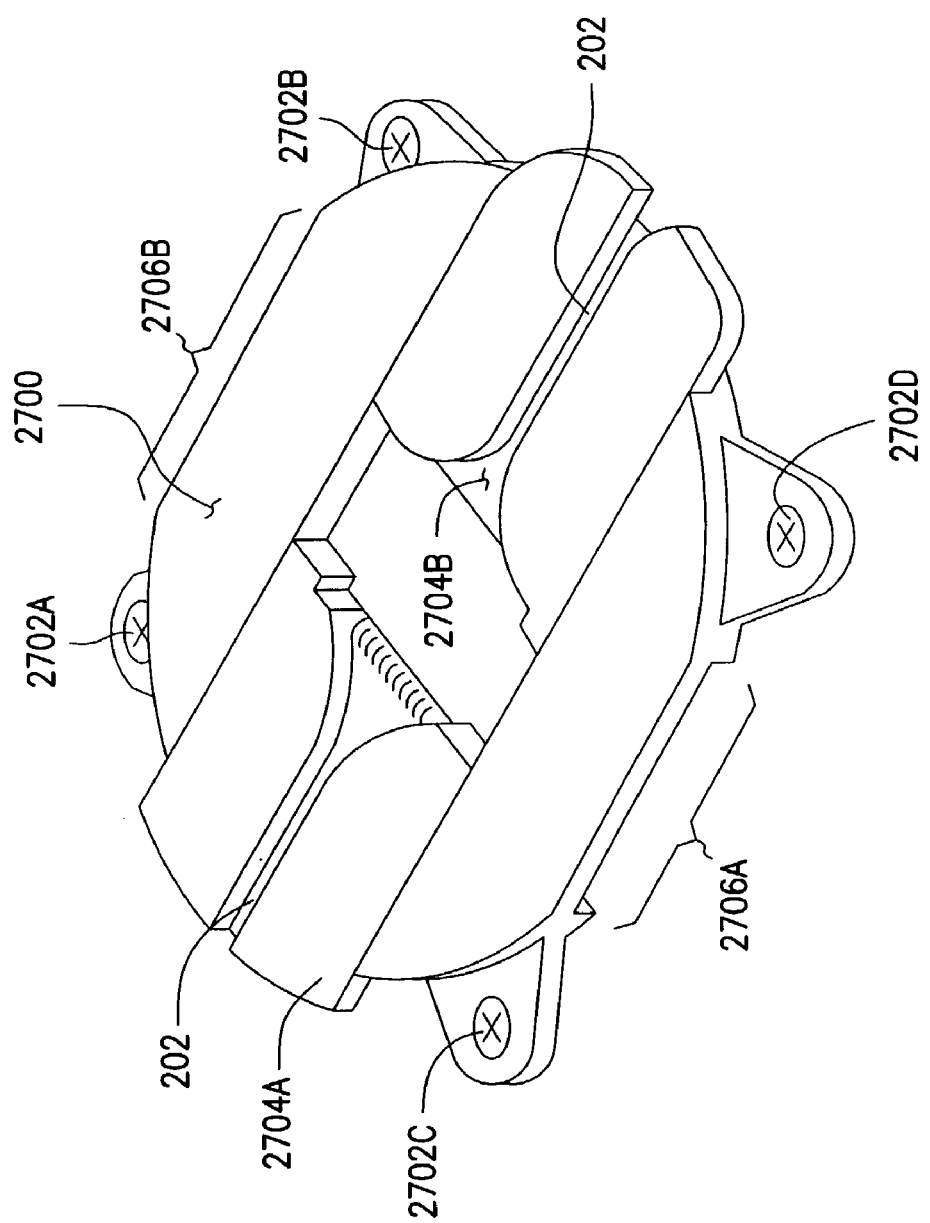
FIG. 27 is a perspective view alternate example of an instrument-securing base.

FIG. 27 is a perspective view of an alternate example of an instrument-securing base 2700. In this example, base 2700 is centered around burr hole 106 and secured to the skull using bone screws 2702A–D extending through openings in leg portions. Base 2700 includes two opposing mating slides 2704A–B that move toward and away from each other, and that mate and engage each other to clamp electrode 100 or other instrument therebetween. One or more slots 202 are provided for providing a lateral exit for electrode 100, as discussed above. Other equipment is either attached directly to the skull around base 2700, or attached indirectly to the skull, though base 2700, such as by snapping or clamping such equipment to receiving sides 2706A–B.

Figure 28:
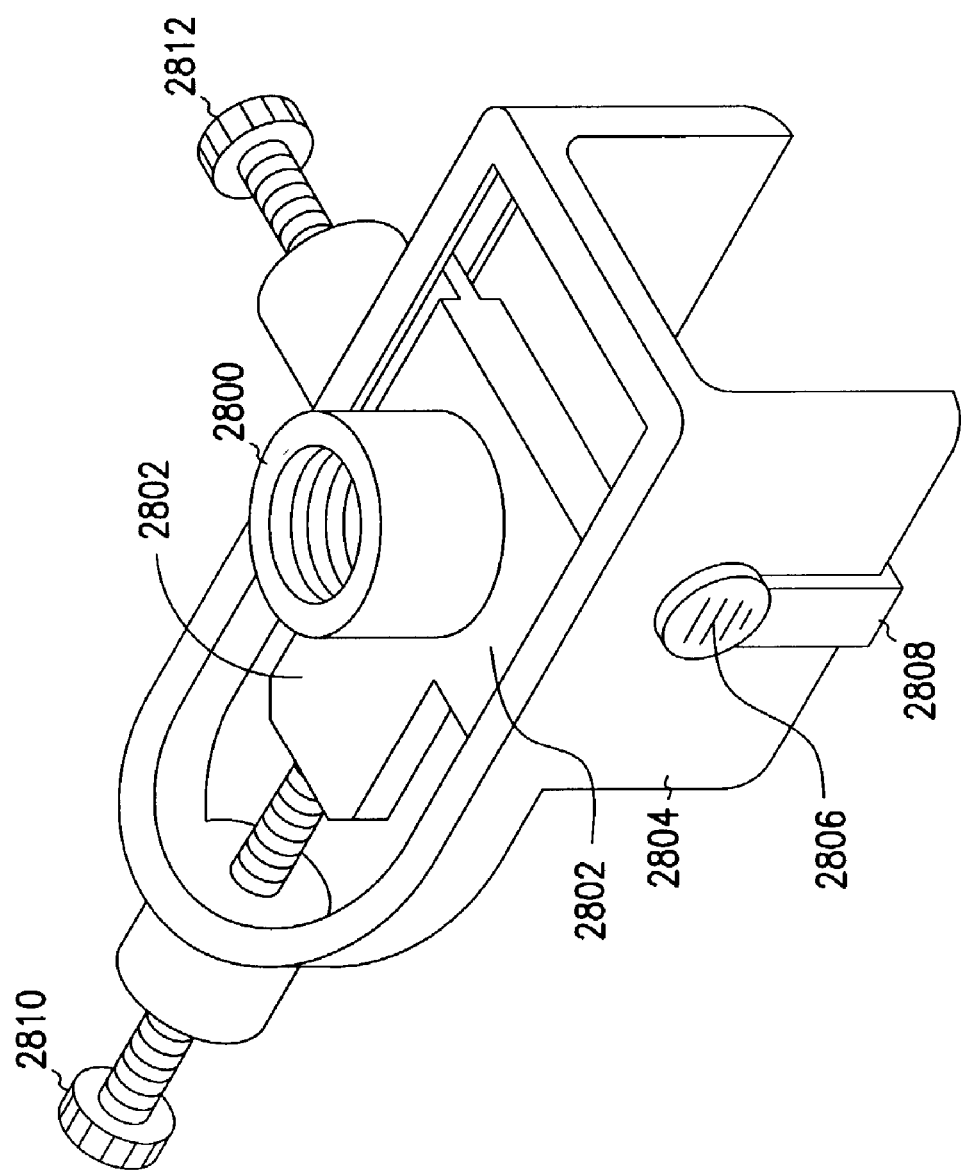
FIG. 28 is a perspective view example of a ball-housing socket on a translational stage.

FIG. 28 is a perspective view of a ball-housing socket 2800, used as an alternative to socket 1114. In this example, socket 2800 rides on a sliding translational stage 2802 on a mount 2804 coupled to saddle 1106 or other portion of deep brain access device 1100. This example includes a squeeze release 2806 for disengaging mount 2804 from saddle 1106 or other affixation point of deep brain access device 1100. Alternatively, mount 2804 is affixed to securing base 2700 by a hooked engagement mechanism 2808 that engages an underside of securing base 2700, or by using any other appropriate coupling technique. Thumbscrew 2810 engages a threaded opening in mount 2804 and also engages and controls translational movement of sliding stage 2802. Thumbscrew 2812 engages a threaded opening in mount 2804 and secures the position of stage 2802 to prevent unwanted translational movement after its desired position is obtained. Either thumbscrew may be captured to prevent accidental separation from mount 2804.

Figure 29:
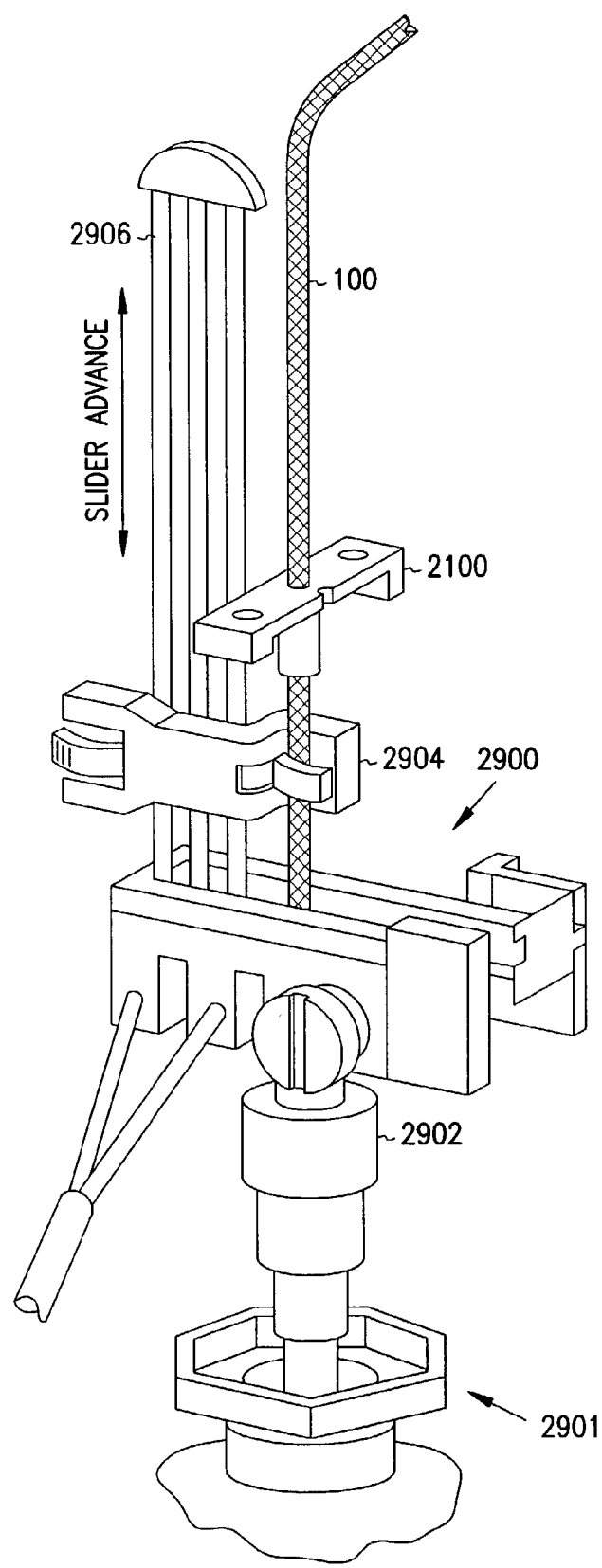
FIG. 29 is a perspective view example of an alternate remote introducer mounted to a deep brain access device.

FIG. 29 is a perspective view illustrating a remote introducer 2900, provided as an alternative to introducer 2500. In this example, introducer 2900 is coupled to a portion of deep brain access device 2901, such as by using a Touhy-Borst adapter 2902 threaded onto a lip of a guide tube, similar to lip 2206 of guide tube 2202. In this example, electrode 100 is inserted through a peel-away sheath 2100 (after removing a stylet). Sheath 2100 is secured to a squeeze-release clamp 2904 that slides toward and away from the skull along slide 2906. In this example, advancement and retraction of clamp 2904 is remotely controlled using controls 2506A–B.

Figure 30:
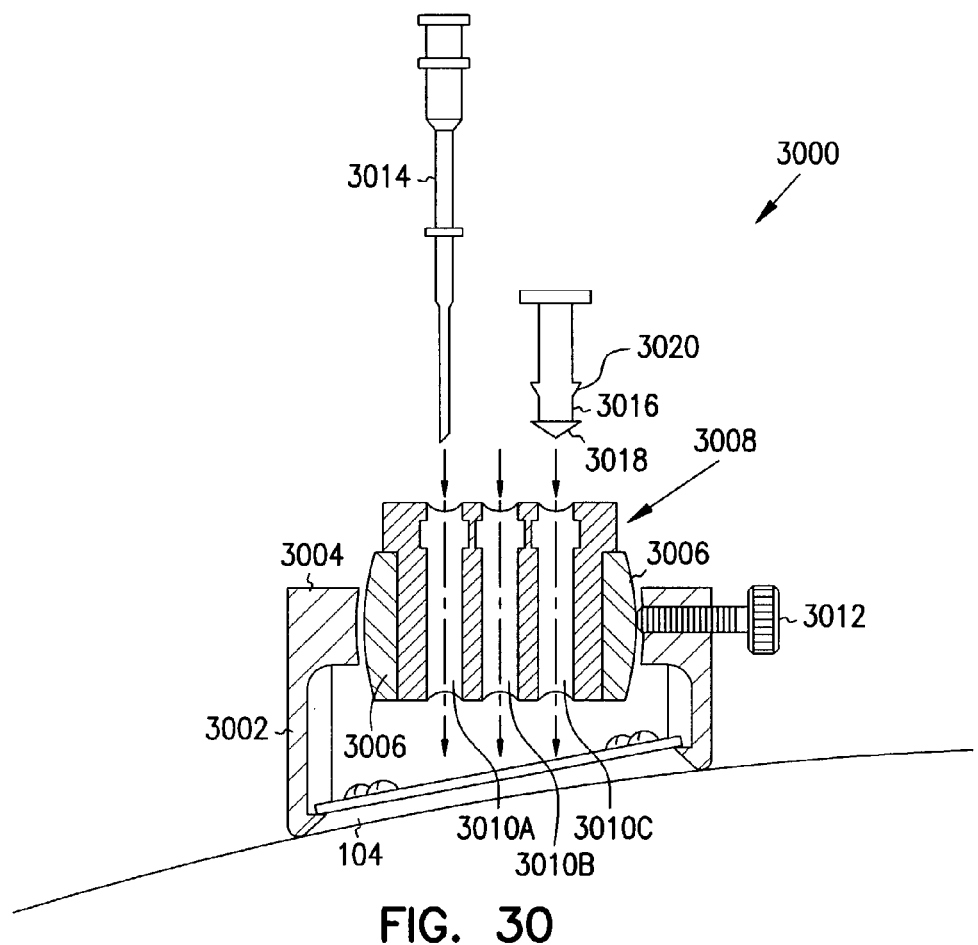
FIG. 30 is a cross-sectional view example of an alternate deep brain access device.

FIG. 30 is a cross-sectional view illustrating a deep brain access device 3000, provided as an alternative to deep brain access device 1100. In this example, base 104 is secured to the skull using bone screws. A pedestal or tower 3002 is secured to base 104 as illustrated or, alternatively, is secured directly to the skull. Tower 3002 includes a socket 3004 housing a ball 3006. Ball 3006 includes a center opening that receives a rotating inner barrel sleeve 3008. In this example, sleeve 3008 includes one or more lumens 3010A–C extending therethrough for passing and guiding instruments, sheaths, stylets, etc. An affixation device, such as thumbscrew 3012, fixes the position of ball 3006 when the desired trajectory alignment has been obtained, such as by using the MRI, CT, PET, or frameless navigational guidance techniques discussed above. Proximal portions of lumens 3010A–C include recesses for snapping into place lips on devices inserted therein, such as alignment stem (or frameless adapter) 3014 and/or Luer stem 3016. A remote introducer may be attached to Luer stem 3016, as discussed above. Luer stem 3016 may include a wedge 3018, for assisting in splitting a peel-away sheath inserted through corresponding lumen 3010 before Luer stem 3016 is inserted therein. Luer stem 3016 may also include orientation tabs 3020 to appropriately align the wedge to provide the desired assistance in splitting the peel-away sheath.

Figure 31:
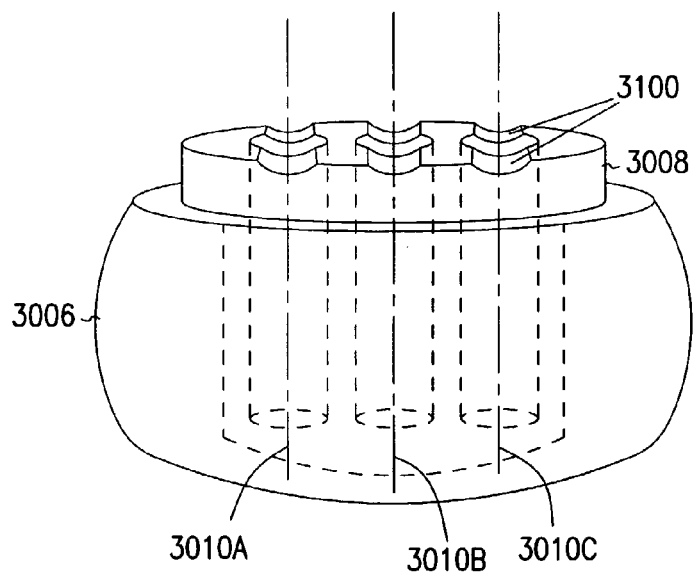
FIG. 31 is a perspective view example of a ball and inner sleeve with guide lumens.

FIG. 31 is a perspective view illustrating an example of ball 3006 and sleeve 3008, including an illustration of the ball-and-socket movement of ball 3006 and rotational movement of sleeve 3008 within ball 3006. In this example, lumens 3010 include associated transverse grooves 3100 extending laterally in opposite directions from the lumens 3010 to opposing edges of sleeve 3008. Grooves 3100 receive and/or hold peel-away portions of one or more peel-away sheaths inserted into respective lumens 3010.

Figure 32A:
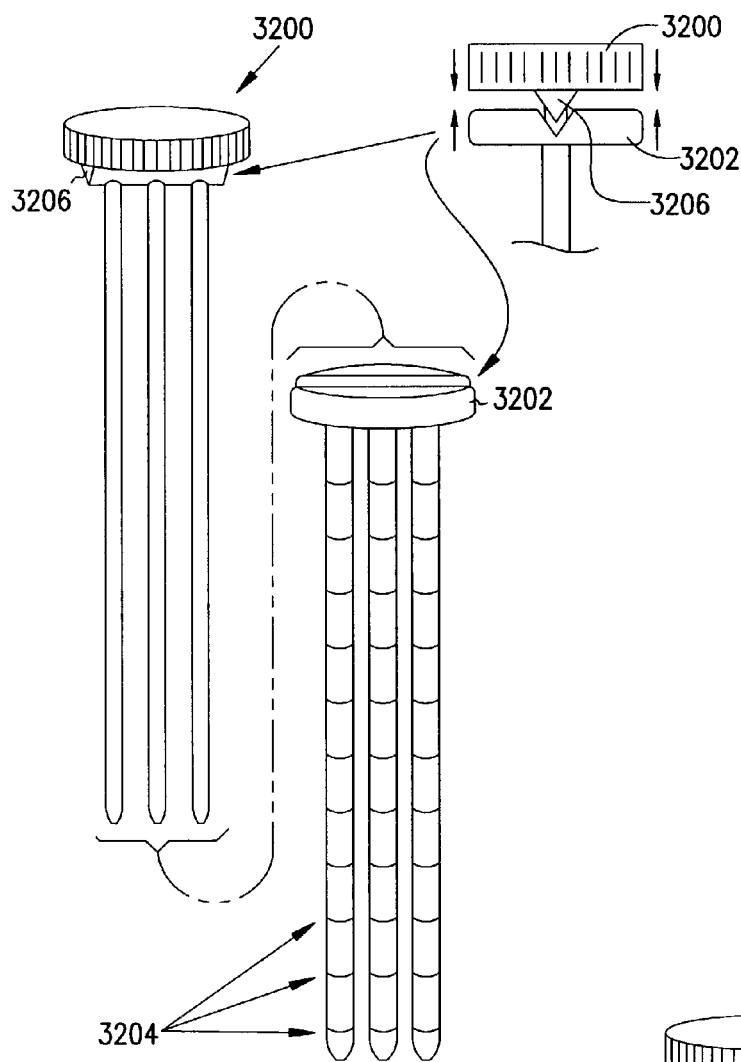
FIG. 32 provides various perspective and cross-sectional view examples of a peel-away sheath with depth markers, a stylet, and a deep brain access device receiving the sheath and stylet.
Figure 32B:
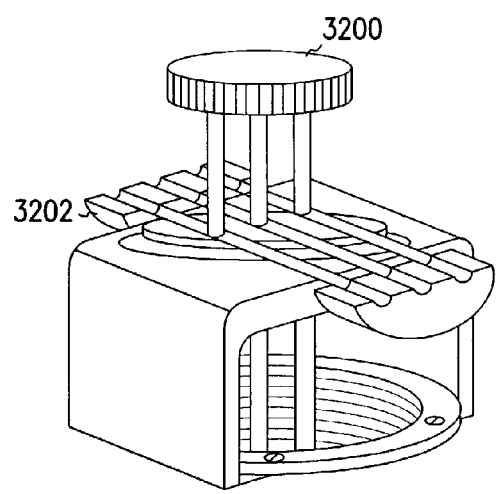

FIG. 32 provides various perspective and side views of portions of deep brain access device 3000 and associated components. In this example, a three prong titanium stylet 3200 assembly is inserted into corresponding lumens of a triple peel-away plastic sheath 3202 assembly. One or more prongs of sheath 3202 includes depth markers 3204. The combined sheath 3202 and stylet 3200 is inserted into corresponding lumens 3010 of guide sleeve 3008 to the desired depth, as indicated by depth markers 3204 on sheath 3202. The proximal portion of sheath 3202 is then separated as illustrated in FIG. 32 and flattened out laterally. Wedge 3206 on a proximal handle portion of stylet 3200 may assist in splitting sheath 3202. This establishes the prongs of sheath 3202 at the desired depth. Stylet 3200 is then removed, and electrode 100 or another instrument is introduced into position through the sheath 3202.

Figure 33B:
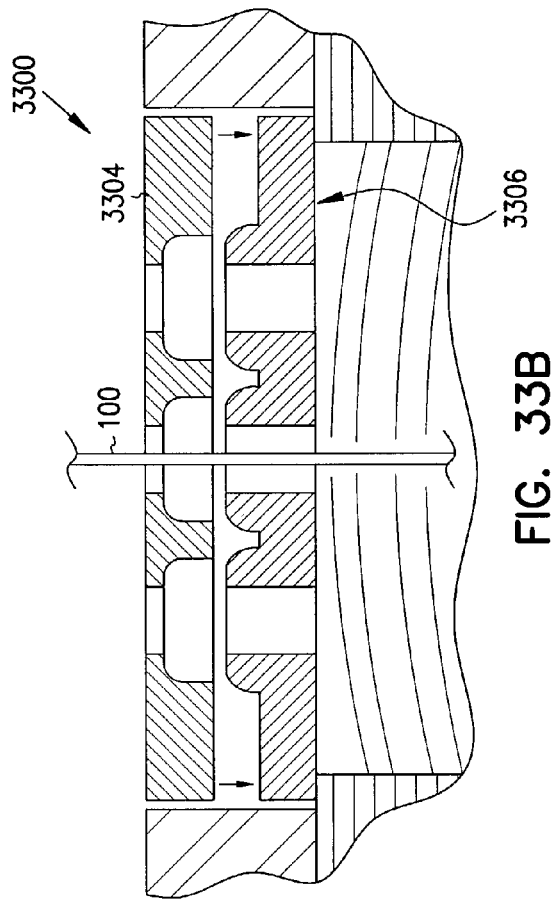
FIG. 33 provides various perspective and cross-sectional view examples of an alternate stabilizer.
Figure 33A:
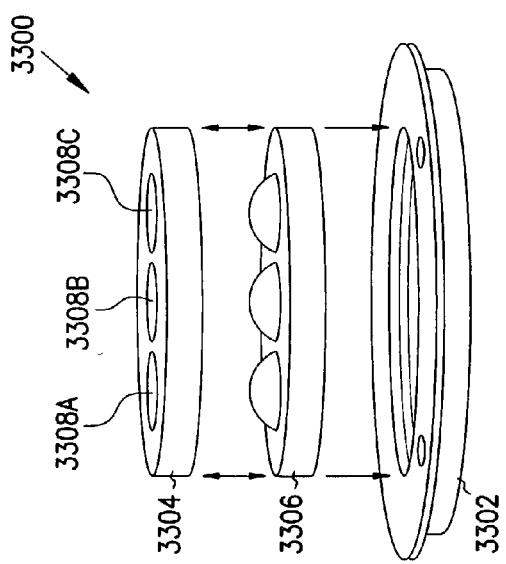
Figure 33C:
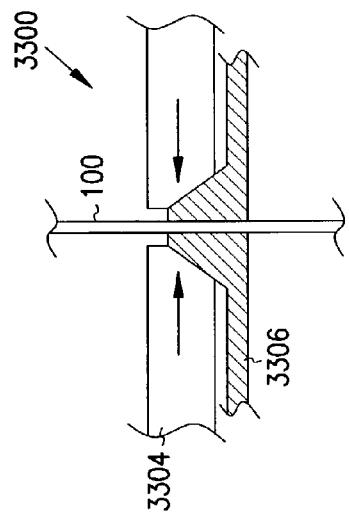

FIG. 33 provides exploded perspective and cross-sectional views of a stabilizer 3300, which can serve as an alterative to stabilizer 110. In this example, stabilizer 3300 includes a substantially rigid ring-like base 3302, a substantially rigid upper plate, 3304, and a soft middle plate 3306 interposed between upper plate 3304 and lower ring 3302. Upper plate 3304 and middle plate 3306 include corresponding openings 3308. A neurostimulating electrode 100 or other instrument is passed through one of these openings 3308. A soft male protuberance around the opening in middle plate 3306 is received within a female receptacle around the opening in upper plate 3304. When upper plate 3304 is clamped down against base 3302, the soft protuberance is squeezed against the electrode 100, holding it securely in place.

FIG. 34 is a perspective view of an stabilizer 3400, which provides an alternative to stabilizer 110. In this example, stabilizer 3400 is rubber or any other flexible material that tends to return to its original shape. A spreader 3402 is used to open a slot 3406 in stabilizer 3400, which is then inserted into an instrument-securing base-plate fastened to the skull. When electrode 100 or other instrument is properly positioned, the spreader is removed, allowing stabilizer 3400 to return to its original shape with the slot 3406 closed around the electrode 100 to hold it securely in place.

Figure 35:
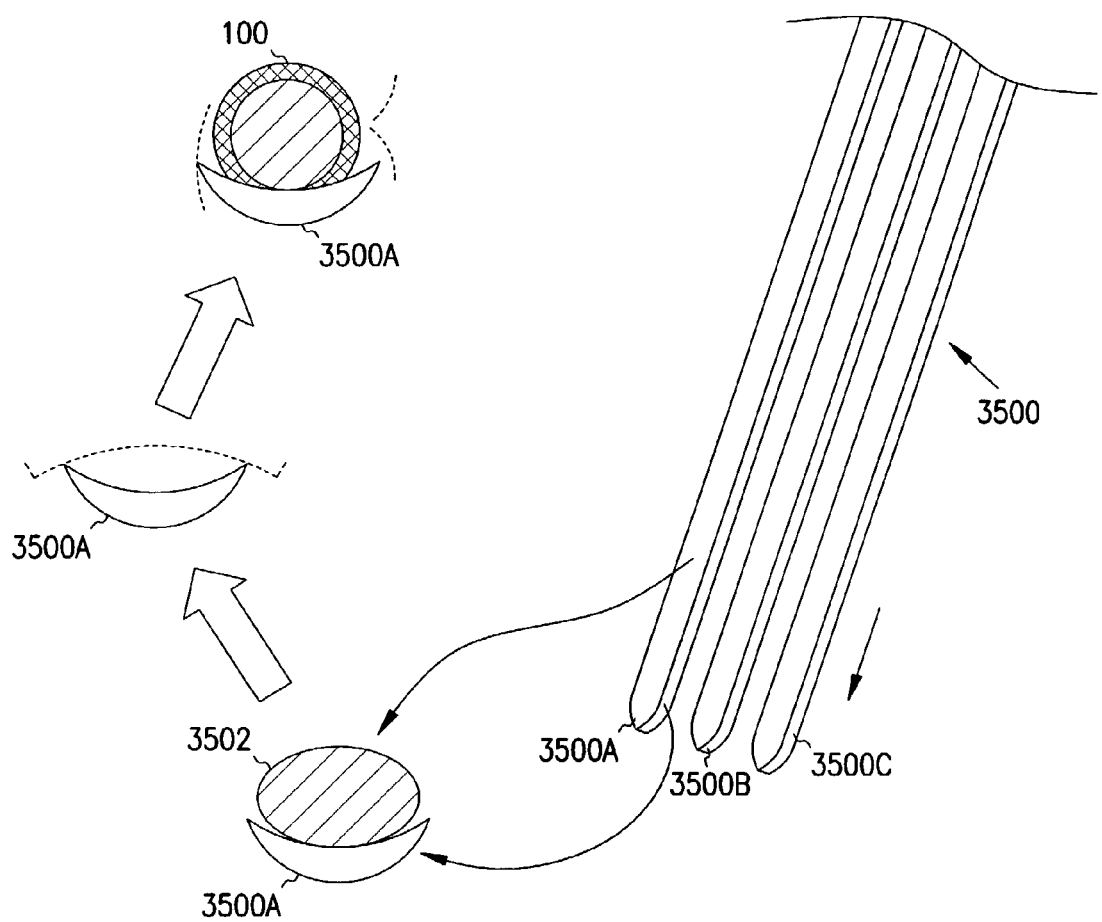
FIG. 35 provides various perspective and cross-sectional view examples of a guide alternative to the peel-away sheaths.

FIG. 35 provides a perspective view and several cross-sectional views illustrating a sheath-substitute guide 3500, which provides an alternative to the peel-away sheaths discussed above. In this example, guide 3500 includes one or more elongate guides 3500A–C that do not have a central bore lumen for guiding an instrument through. Instead, each guide 3500A–C includes a cross-section that is formed for guiding an instrument along its side. In this example, the cross-section is crescent-shaped so as to provide a degree of mating to the outer diameter of electrode 100, stylet 3502, or other instrument that is introduced into the patient along the side of the guide 3500. In one example, guide 3500 is introduced in tandem with removable stylet 3502, which provides additional rigidity to the introduction process. In another example, guide 3500 is introduced without removable stylet 3502. Because guide 3500 does not use a central bore lumen, coring of brain tissue during its introduction may be of less concern. Guide 3500 allows access to the adjacent electrode 100 along its entire length, allowing electrode 100 to be gripped and/or secured very close to the skull (such as using instrument-securing base 104) before guide 3500 is removed. This prevents excessive movement of electrode 100 during extraction of guide 3500, which provides more accurate placement of electrode 100 or other instrument.

Figure 36:
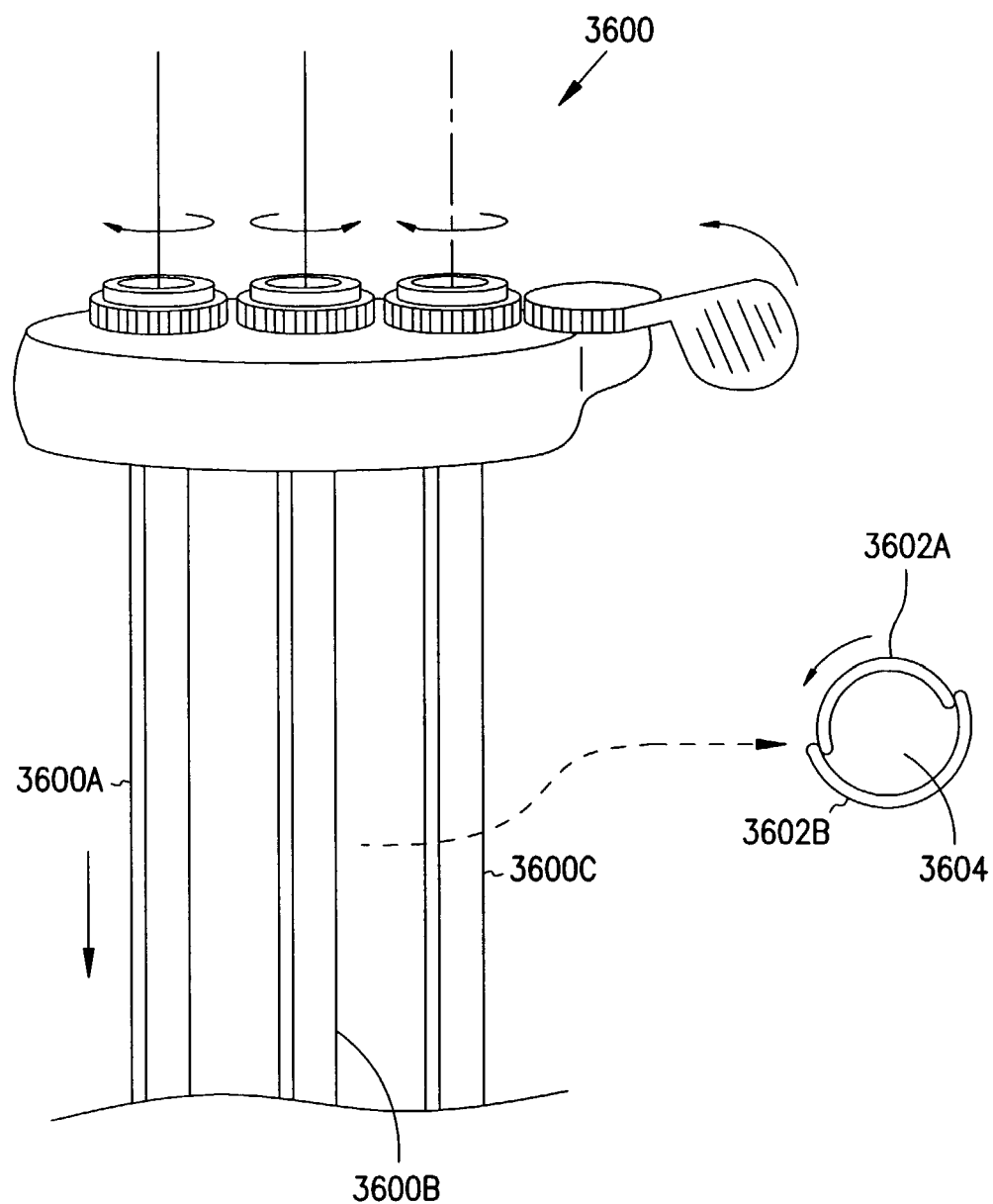
FIG. 36 provides a perspective and a cross-sectional view examples of a sheath having rotatable components for allowing side access, which is useful as an alternative to the peel-away sheath.

FIG. 36 provides a perspective view and a cross-sectional view illustrating a sheath 3600 assembly, which provides another alternative to the peel-away sheaths discussed above. In this example, sheath 3600 assembly includes one or more elongate sheaths 3600A–C. Each elongate sheath 3600 includes an open slot along its length, or a portion thereof. In the illustrated example, each elongate sheath 3600 includes two C-shaped portions 3602A–B that rotate with respect to each other by manipulating a handle portion of the sheath 3600. When the C-shaped portions 3602A–B are rotated into a closed position, they together effectively provide a central lumen 3604 through which electrode 100 or other instrument may be passed. When the C-shaped portions 3602A–B are rotated into an open position, they together effectively provide an open slot along their length, allowing access to electrode 100 or other instrument that has been inserted therethrough. This allows electrode 100 to be gripped and/or secured very close to the skull (such as using instrument-securing base 104) before sheath 3600 is removed. This prevents excessive movement of electrode 100 during extraction of sheath 3600, which provides more accurate placement of electrode 100 or other instrument. In this example, stylet(s) may be inserted into the lumen 3604 before sheath 1600 is introduced, to avoid coring of brain tissue.

Figure 37:
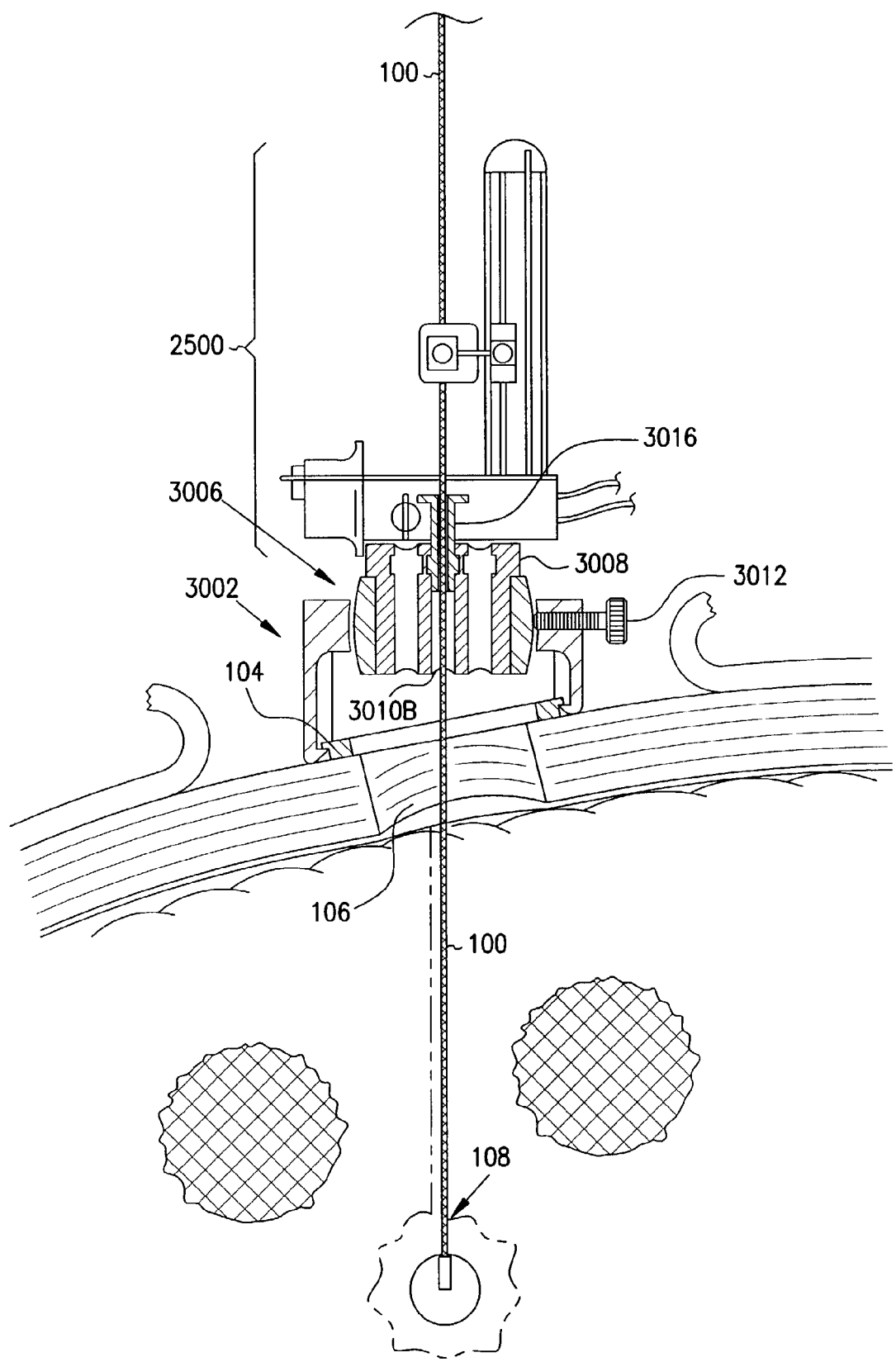
FIG. 37 is a cross-sectional view example of an alternative deep brain access device, mounted to a skull, and a remote introducer mounted to the deep brain access device.

FIG. 37 is a cross-sectional view illustrating an example of deep brain access device 3000 mounted onto the patient's skull with remote introducer 2500 mounted onto Luer stem 3016, which is snapped into central lumen 3010B. Neurostimulating electrode 100 is held by introducer 2500, and passed through central lumen 3010B to target location 108 of the brain.

Figure 38:
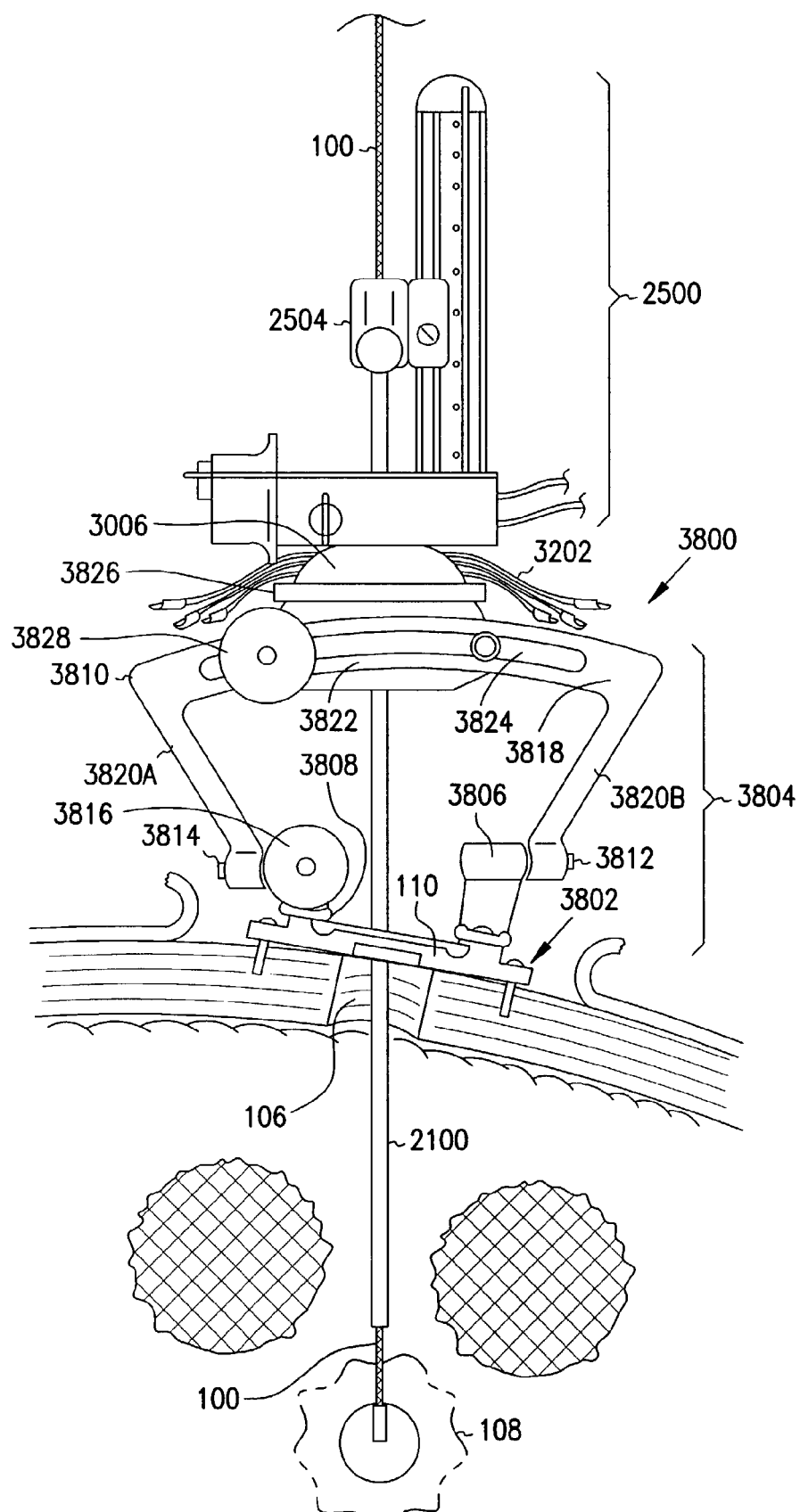
FIG. 38 is a perspective view example of an alternative deep brain access device providing a pivoting base, an arc-like path, and a ball-and-socket movement for adjusting a trajectory of an instrument being introduced into the brain.

FIG. 38 is a cross-sectional view illustrating an alternate example of a deep brain access device 3800. This example illustrates a base 3802, which is centered around burr hole 106 and secured to the skull. A tower 3804 is secured to base 3802 or, alternatively, directly to the skull. Tower 3804 includes mounting legs 3806 and 3808, which are affixed to base 3802 or to the skull. The mounting legs 3806 and 3808 are coupled to a pedestal 3810 by pivot pins 3812 and 3814. Pins 3812 and 3814 are aligned to provide a longitudinal axis about which pedestal 3810 pivots until locked in place by thumbscrew 3816, which engages one of the pins 3812 and 3814. Thus, pedestal 3810 would be capable of pivoting into and out of the drawing of FIG. 38.

In the example of FIG. 38, pedestal 3810 includes an arc 3818 extending between leg extensions 3820A–B that are coupled to pivot pins 3812 and 3814. Arc 3818 is curved, so that a center portion 3822, away from leg extensions 3820A–B, would be more distant from the viewer of FIG. 38 than the portions of arc 3818 that are closer to leg extensions 3820A–B. Arc 3818 includes a slot 3824 extending substantially along its length between leg extensions 3820A–B. A socket 3826 engages and rides along slot 3824, until locked into position by securing thumbscrew 3828 against arc 3818. Socket 3826 houses a ball 3006 that can be adjusted spherically until locked into place by one or more thumbscrews. Ball 3006 includes a center sleeve 3008 having one or more lumens, as discussed above with respect to FIG. 30. In the example of FIG. 38, a Luer stem 3016 is snapped into a center lumen of sleeve 3008, and a remote introducer 2500 is mounted onto the Luer stem for guiding electrode 100 to target location 108.

Figure 39:
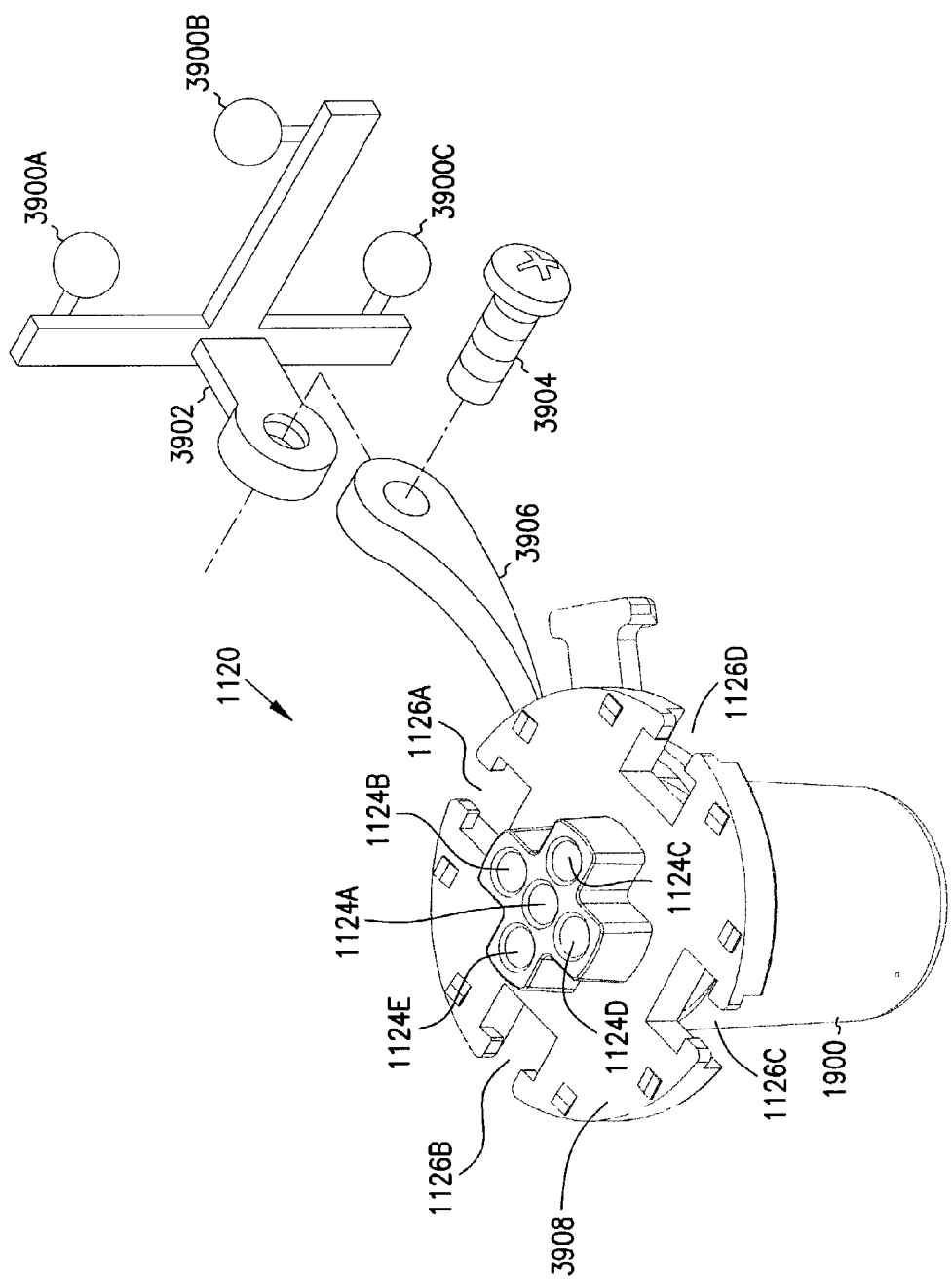
FIG. 39 is a perspective view illustrating an alternate example of a multilumen insert including imaging-recognizable fiducial markings.

FIG. 39 is a perspective view illustrating an alternate example of a multilumen insert 1120. In this example, multilumen insert 1120 includes one or more fiducial markers 3900A–C (e.g., LEDs, reflective globes, or MRI-imagable microcoils), such as for trajectory alignment in a frameless surgical navigation system or in an MRI environment. This illustration shows three such imagable fiducial markers 3900A–C defining a plane. Fiducials 3900A–C are supported on respective arms extending from an attachment extension 3902, which is coupled by an fastener, such as screw 3904, to an aim 3906 that extends upward and outward from the planar face plate 3908 of multilumen insert 1120. This coupling is performed (e.g., using integral alignment guides or, alternatively, performing a calibration adjustment) so that a predetermined known spatial relationship exists between the plane formed by imagable fiducials 3900A–C and the plane of face plate 3908, which is orthogonal to the instrument trajectory axis through each of lumens 1124A–E. Consequently, imaging fiducials 3900A–C are viewed in conjunction with adjusting the various positioning mechanisms of the deep brain access device to obtain and fix the desired instrument trajectory with respect to the entry portal. Although, in this example, imaging fiducials 3900A–C are illustrated as being attached and in a known spatial relationship to plate 3908, imaging fiducials 3900A–C may alternatively be attached to any other component of the deep brain access device so as to establish a known spatial relationship between the fiducials 3900A–C and an axial trajectory provided by one or more of lumens 1124A–E. As another alternative, any component of the deep brain access device includes an adapter for receiving one of several commercially available surgical navigation instruments. Such surgical navigation instruments similarly provide imaging-recognizable fiducials. Such an adapter should be oriented such that the spatial relationship between the surgical navigation instrument and the instrument trajectory is known, thereby allowing imaging of the fiducials to assist in adjusting the trajectory to target location 108.

The discussed devices and methods may be used in with frameless surgical navigation or with MRI or other imaging. Such techniques permit real-time determination and confirmation of anatomical placement of the instrument for improving targeting and placement accuracy. Other advantages include, among other things, an alignment apparatus that uses a localized coordinate system in which positioning and aligning is based on a coordinate system relative to the patient's skull and the skull entry point rather than a stereotactic frame; real-time imaging that eliminates the need for retrospective imaging and also allows direct confirmation of the anatomical placement; an anatomically determined initial targeting angle (the angle between the body or skull surface and the theoretical target) that is selected based on the patient's actual anatomy; a unique center-of-arc principle using rotation about the nominal trajectory axis, thus simplifying optimization of the first angular adjustment; a locking ball-and-socket arrangement for easy and accurate direct targeting under real-time imaging or frameless surgical navigation; peel-away or alternative sheaths that allow the device to be easily secured into position; access to the base plate assembly so that the electrode can be captured at the surface of the skull immediately after successful placement and before disassembly of the targeting apparatus; and visible (under the imaging method chosen, e.g., under CT or MRI) alignment stems.

Similarly, the stabilization system provides for in situ stabilization immediately upon proper placement, through use of a disk and cam arrangement, thus eliminating inadvertent movement during disassembly of the alignment apparatus, and reducing the likelihood of the electrode moving after implantation; the snap-fit solid cap protects the electrode and its capture mechanism from damage; the stabilization system is substantially scaled to minimize ingress and egress; the base plate is securely attached to the body; a special tool facilitates placement of the base plate correctly into the burr hole, thus assuring adequate clearance for proper assembly of all parts, as well as pre-positioning apparatus for easy attachment; and the electrode is captured by clamping it in a gap between two parts, therefore electrode damage cannot occur because the gap size is limited by a physical stop.

Although the examples primarily discuss targeting, placement, and stabilization of a deep brain electrode, this is just an example of one of the possible procedures that can be done using the body portal type trajectory guide. Numerous other procedures will be accomplished using this device. In addition, the device will give rise to other future surgical procedures.

It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein.

What is claimed is:

1. An access device for guiding an instrument along a trajectory through an entry portal in a surface, the entry portal defining an entry plane and a rotation axis normal to the entry plane, the access device including:
   a base, configured to be mounted to the surface in or about the entry portal;
   an instrument guide assembly, rotatably coupled to the base to allow rotation of the instrument guide assembly about the rotation axis;
   an instrument guide, including at least one first guide lumen for guiding the instrument, the at least one first guide lumen defining a corresponding at least one first insertion axis, the instrument guide coupled to the instrument guide assembly using an arc-shaped sliding joint capable of adjusting an insertion angle of the at least one insertion axis with respect to the rotation axis; and
   wherein the base and the instrument guide assembly are sized and shaped to allow viewing of the entry portal during the insertion of the instrument through the entry portal as directed by the instrument guide.

2. The access device of claim 1, wherein the base and the instrument guide assembly are sized and shaped to allow access to the instrument during the insertion of the instrument through the entry portal as directed by the instrument guide.

3. The access device of claim 1, in which the instrument guide includes at least one second guide lumen for guiding the instrument, the at least one second guide lumen defining a corresponding at least one second insertion axis.

4. The access device of claim 3, in which the at least one first guide lumen is offset from the at least one second guide lumen by a predetermined distance.

5. The access device of claim 4, in which the at least one first insertion axis is parallel to the at least one second insertion axis.

6. The access device of claim 3, in which the first and second guide lumens are both sized for receiving a reference device for aligning the trajectory with a target, the reference device including at least one locator.

7. The access device of claim 6, further including the reference device for aligning the trajectory with the target, the reference device including at least one locator.

8. The access device of claim 7, in which at least one locator includes at least one light emitting diode.

9. The access device of claim 7, in which the at least one locator includes at least one light reflector.

10. The access device of claim 7, in which at least one locator includes at least one electrically-conductive coil.

11. The access device of claim 6, in which the reference device includes a pair of locators defining the trajectory along the one of the first and second insertion axes corresponding to one of the first and second guide lumens into which the reference device is inserted.

12. The access device of claim 3, further including a lumen selector device that, when coupled to the instrument guide, provides a selecting lumen defining a selecting axis that is aligned to be collinear with one of the first and second insertion axes.

13. The access device of claim 3, further including a lumen selector device that, when coupled to the instrument guide, provides a selecting lumen that is aligned with one of the first and second guide lumens.

14. The access device of claim 1, in which the instrument guide includes a detachable multilumen insert, the multilumen insert including a plurality of guide lumens that are sized and shaped for guiding the instrument.

15. The access device of claim 14, in which the instrument guide includes a lateral adjustment device that is configured to laterally adjust locations of the guide lumens in a direction that is substantially orthogonal to the first insertion axis.

16. The access device of claim 15, in which the lateral adjustment device includes:
a socket;
a ball at least partially in the socket; and
at least one screw through the socket that engages the ball to adjust a location of the ball with respect to the socket.

17. The access device of claim 1, in which the instrument guide includes a lateral adjustment device that is configured to laterally adjust locations of the guide lumens in a direction that is substantially orthogonal to the first insertion axis.

18. The access device of claim 17, in which the lateral adjustment device includes:
a socket;
a ball at least partially in the socket; and
screws through the socket to engage the ball to adjust a location of the ball with respect to the socket.

19. An access device for guiding an instrument along a trajectory though an entry portal in a surface, the entry portal defining an entry plane and a rotation axis normal to the entry plane, the access device including:
a base, configured to be mounted to the surface in or about the entry portal; and
an instrument guide, adjustably coupled to the base for adjusting and fixing the trajectory, the instrument guide including a plurality of guide lumens arranged in a predetermined spatial relationship, the guide lumens including:
a central guide lumen, defining a central insertion axis that intersects the rotation axis at the entry plane; and
four peripheral guide lumens, offset from the central guide lumen, the peripheral guide lumens defining corresponding peripheral insertion axes that are parallel to the first insertion axis.

20. The access device of claim 19, farther including a lumen selector device including a selecting lumen, the lumen selector device being couplable to the instrument guide such that the selecting lumen is aligned with one of the guide lumens.

21. The access device of claim 20, in which the lumen selector device is couplable to the instrument guide in a plurality of orientations, including a first orientation and a second orientation, the first orientation aligning the selecting lumen to a different one of the guide lumens than the second orientation.

22. The access device of claim 19, in which the guide lumens include:
a first guide lumen, defining a first insertion axis that intersects the rotation axis at the entry plane; and
a second guide lumen, defining a second insertion axis that is parallel to the first insertion axis and displaced from the first insertion axis by a predetermined distance.

23. The access device of claim 22, in which the first and second guide lumens are both sized for receiving a reference device for aligning the trajectory with a target, the reference device including at least one locator.

24. The access device of claim 23, further including the reference device for aligning the trajectory with a target, the reference device including at least one locator.

25. The access device of claim 24, in which at least one locator includes at least one light emitting diode.

26. The access device of claim 24, in which the at least one locator includes at least one light reflector.

27. The access device of claim 24, in which at least one locator includes at least one electrically-conductive coil.

28. The access device of claim 24, in which the at least one locator is locatable using an imaging apparatus.

29. The access device of claim 24, in which the reference device includes a pair of locators defining the trajectory along the one of the first and second insertion axes corresponding to one of the first and second guide lumens into which the reference device is inserted.

30. The access device of claim 19, further including at least one lumen selector device including at least one selecting lumen, the lumen selector device being couplable to the instrument guide such that the selecting lumen aligns with only one of the guide lumens.

31. The access device of claim 30, in which the at least one lumen selector device includes:
a central lumen selecting bridge, including a first selecting lumen, the first central lumen selecting bridge being couplable to the instrument guide such that the selecting lumen always aligns with the central guide lumen; and a peripheral lumen selecting bridge, including a second selecting lumen, the peripheral lumen selecting bridge being couplable to the instrument guide in a selected orientation of a plurality of orientations such that the selecting lumen aligns with a single one of the peripheral lumens based on the selected orientation.

32. The access device of claim 19, further including:
an instrument guide assembly, carrying the instrument guide, the instrument guide assembly coupled to the base to allow rotation of the instrument guide assembly about the rotation axis; and
wherein the instrument guide includes a first guide lumen defining a first insertion axis that intersects the rotation axis at the entry plane, and wherein the instrument guide is coupled to the instrument guide assembly using an arc-shaped sliding joint capable of adjusting an insertion angle of the at least one insertion axis with respect to the rotation axis.

33. The access device of claim 19, wherein the base and the instrument guide assembly are sized and shaped to allow viewing of the entry portal during the insertion of the instrument through the entry portal as directed by the instrument guide.

34. The access device of claim 19, in which the instrument guide includes a lateral adjustment device that is configured to laterally adjust locations of the guide lumens in a direction that is substantially orthogonal to the trajectory.

35. The access device of claim 34, in which the lateral adjustment device includes:
a socket;
a ball at least partially in the socket; and
at least one screw through the socket that engages the ball to adjust a location of the ball with respect to the socket.

36. A method including:
securing a base portion of a multiple guide lumen carrying assembly around an entry portal in a surface;
rotating at least a portion of the guide lumen carrying assembly about a first axis that is substantially concentric to the entry portal and substantially orthogonal to the surface;
tilting at least a portion of the assembly so that a second axis, extending concentrically through one of the guide lumens in the guide lumen carrying assembly, is at a desired angle with the entry portal in the surface; and
fixing a position of the guide lumen, including securing the rotating portion of the guide-lumen assembly and securing the tilting portion of the guide-lumen carrying assembly in a manner to allow viewing of the entry portal during insertion of an instrument through the entry portal as directed by the guide lumen of the instrument guide.

37. The method of claim 36, further including introducing an instrument through the one of the guide lumens along a trajectory provided by the second axis.

38. The method of claim 36, further including receiving, into the one of the guide lumens, a portion of a remotely locatable alignment device for performing the rotating and the tilting using computer-assisted visualization of a target region located beyond the entry portal.

39. The method of claim 36, further including introducing an instrument through a different one of the guide lumens than the one of the guide lumens defining the second axis.

40. The method of claim 36, further including concentrically aligning the base portion to the entry portal.

41. The method of claim 40, in which the aligning includes:
inserting a screw-carrying positioner through an opening in the base portion and into the entry portal to position the base portion concentrically around the entry portal;
screwing the base portion to the surface, thereby releasing the screws from the screw-carrying positioner; and
removing the positioner.

42. The method of claim 36, further including introducing an instrument through the one of the guide lumens and the entry portal toward a target location beyond the surface of the entry portal.

43. The method of claim 42, in which the guide lumen is a first guide lumen, and further including reintroducing the instrument through a second guide lumen offset from the first guide lumen by a predetermined distance, the second guide lumen concentrically defining a third axis that is parallel to the second axis through the first guide lumen.

44. The method of claim 36, further including selecting a particular one of the guide lumens for introducing an instrument by at least one of orienting and coupling a guide lumen selector to the guide lumen carrying assembly.

45. The method of claim 36, further including laterally displacing the guide lumens in a direction that is substantially orthogonal to the second axis.

* * * * *